(12) United States Patent
Robl

(10) Patent No.: US 6,620,821 B2
(45) Date of Patent: Sep. 16, 2003

(54) HMG-COA REDUCTASE INHIBITORS AND METHOD

(75) Inventor: Jeffrey A. Robl, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/008,154

(22) Filed: Dec. 4, 2001

(65) Prior Publication Data

US 2002/0061901 A1 May 23, 2002

Related U.S. Application Data

(63) Continuation-in-part of application No. 09/875,218, filed on Jun. 6, 2001, now abandoned.
(60) Provisional application No. 60/211,594, filed on Jun. 15, 2000.

(51) Int. Cl.⁷ .................... A61K 31/435; A61K 31/473; C07D 221/06; C07D 405/06; A61P 3/06
(52) U.S. Cl. ..................... 514/290; 546/93; 546/101; 546/111
(58) Field of Search ............. 546/93, 101, 111; 514/290

(56) References Cited

U.S. PATENT DOCUMENTS

| | | |
|---|---|---|
| 4,906,624 A | 3/1990 | Chacholowski et al. |
| 4,925,852 A | 5/1990 | Keeseler et al. |
| 5,006,530 A | 4/1991 | Angerbauer et al. |
| 5,169,857 A | 12/1992 | Angerbauer et al. |
| 5,177,080 A | 1/1993 | Angerbauer et al. |
| 5,686,433 A | 11/1997 | Robl |

FOREIGN PATENT DOCUMENTS

| | | |
|---|---|---|
| EP | 0306929 A2 | 3/1989 |
| EP | 0307342 A2 | 3/1989 |
| EP | 0325129 A2 | 7/1989 |
| EP | 0325130 A2 | 7/1989 |

OTHER PUBLICATIONS

Robl et al, J. Med. Chem., 34, 2804–2815, 1991.

Primary Examiner—Evelyn Mei Huang
(74) Attorney, Agent, or Firm—Burton Rodney

(57) ABSTRACT

Compounds of the following structure are HMG CoA reductase inhibitors and thus are active in inhibiting cholesterol biosynthesis, modulating blood serum lipids, for example, lowering LDL cholesterol and/or increasing HDL cholesterol, and treating hyperlipidemia, dyslipidemia, hormone replacement therapy, hypercholesterolemia, hypertriglyceridemia and atherosclerosis as well as Alzheimer's disease and osteoporosis

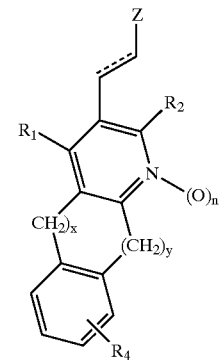

and pharmaceutically acceptable salts thereof, Z is 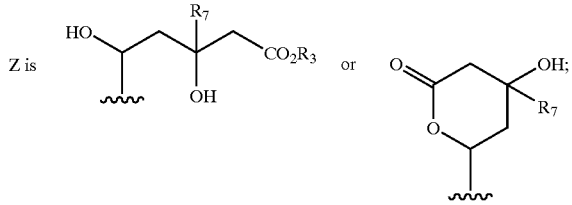

n is 0 or 1;

x is 0, 1, 2, 3 or 4;

y is 0, 1, 2, 3 or 4, provided that at least one of x and y is other than 0; and optionally one or more carbons of $(CH_2)_x$ and/or $(CH_2)_y$ together with additional carbons form a 3 to 7 membered spirocyclic ring;

$R_1$ and $R_2$ are the same or different and are independently selected from alkyl, arylalkyl, cycloalkyl, alkenyl, cycloalkenyl, aryl, heteroaryl or cycloheteroalkyl;

$R_3$ is H or lower alkyl;

$R_4$ and $R_7$ are as defined herein.

18 Claims, No Drawings

HMG-COA REDUCTASE INHIBITORS AND METHOD

This application is a continuation-in-part of U.S. application Ser. No. 09/875,218 filed Jun. 6, 2001, abandoned which application claims priority from U.S. provisional application No. 60/211,594, filed Jun. 15, 2000.

FIELD OF THE INVENTION

The present invention relates to compounds and pharmaceutical compositions useful as hypocholesterolemic and hypolipidemic agents. More particularly, this invention concerns (1) certain inhibitors of the enzyme 3-hydroxy-3-methylglutaryl-coenzyme A reductase (HMG-CoA reductase) that include a pyridine containing nucleus attached by means of a linker to an HMG-binding domain sidechain, (2) pharmaceutical compositions containing such compounds and (3) a method of lowering blood serum cholesterol levels and modulating blood serum lipids employing such pharmaceutical compositions.

BACKGROUND OF THE INVENTION

U.S. Pat. No. 5,686,433 to Robl discloses the structure:

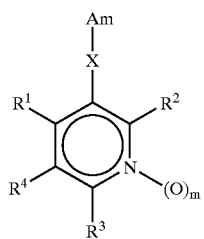

wherein:
Am is a binding domain sidechain;
X is a linker;
$R^1$ and $R^2$ are the same or different and are each independently selected from:
 (i) hydrogen,
 (ii) alkyl,
 (iii) aryl,
 (iv) cycloalkyl,
 (v) aralkyl,
 (vi) aralkoxy,
 (vii) alkenyl,
 (viii) cycloalkenyl, and
 (ix) heterocyclo (e.g., thienyl, benzodioxolyl);
$R^3$ is selected from:
 (i) hydrogen,
 (ii) lower alkyl,
 (iii) aryl,
 (iv) cycloalkyl,
 (v) alkoxy,
 (vi) aralkyl,
 (vii) aralkoxy,
 (viii) alkenyl,
 (ix) cycloalkenyl,
 (x) halo-substituted alkyl,
 (xi) adamantyl, and
 (xii) heterocyclo (e.g., thienyl, benzodioxolyl);
$R^4$ is selected from:
 (i) hydrogen,
 (ii) lower alkyl,
 (iii) aryl,
 (iv) cycloalkyl,
 (v) alkoxy,
 (vi) aralkyl,
 (vii) aralkoxy,
 (viii) alkenyl,
 (ix) cycloalkenyl,
 (x) adamantyl,
 (xi) halogen,
 (xii) halo-substituted alkyl (e.g., trifluoromethyl), and
 (xiii) heterocyclo (e.g., thienyl, benzodioxolyl);
or $R^3$ and $R^4$ taken together can be:

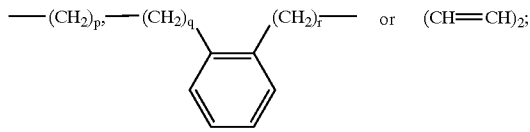

but when $A_m$ is:

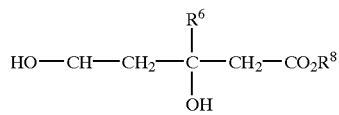

or a δ lactone thereof, $R^3$ and $R^4$ cannot be $(CH=CH)_2$;
$R^6$ is hydrogen or lower alkyl;
$R^8$ is hydrogen, lower alkyl, alkali metal, or alkaline earth metal;
n is 0 or 1;
p is 3, 4 or 5;
q is 0, 1, 2, or 3; and
r is 0, 1, 2, or 3.

In preferred embodiments (Am) is an HMG-binding domain sidechain having a dihydroxy or a phosphinic acid function.

The phosphinic (or phosphonic when X is $CH_2$—O—) acid HMG-binding domain sidechain $(A_1)$ is:

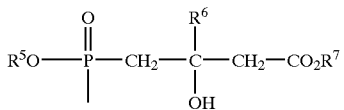

wherein $R^5$ and $R^7$ are independently selected from hydrogen, lower alkyl, alkali metal ion and alkaline earth metal ion; and $R^6$ is hydrogen or lower alkyl.

The dihydroxy acid binding domain sidechain $(A_2$ is:

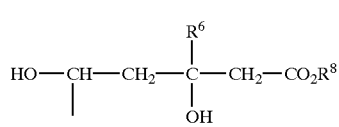

wherein $R^6$ is hydrogen or lower alkyl, $R^8$ is hydrogen or lower alkyl in free acid form or in the form of a physiologically acceptable and hydrolyzable ester or δ lactone thereof (i.e., when Am is:

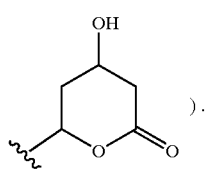

In addition, $R^8$ can be alkali metal ion or alkaline earth metal ion.

A suitable linker (X) is —$(CH_2)_a$—, —CH=CH—, —C≡C—, —$CH_2O$—, wherein O is linked to the phosphorous atom or the aromatic anchor when Am is $A_1$, and wherein O is linked to the aromatic anchor when Am is $A_2$, and wherein "a" is 1, 2, or 3.

BRIEF DESCRIPTION OF THE INVENTION

In accordance with the present invention, there are provided certain pyridine-containing compounds that are potent inhibitors of cholesterol biosynthesis by virtue of their ability to inhibit the enzyme 3-methyl-glutaryl-coenzyme A reductase (HMG-CoA reductase).

In particular, in its broadest chemical compound aspect, the present invention provides compounds of the formula I:

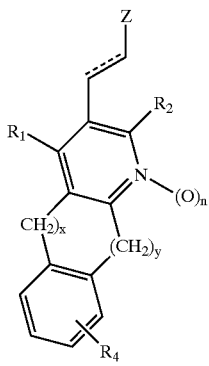

wherein
Z is

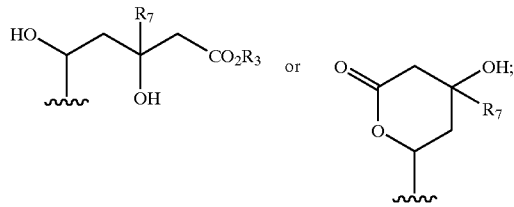

n is 0 or 1;
x is 0, 1, 2, 3 or 4;
y is 0, 1, 2, 3 or 4, provided that at least one of x and y is other then o;
and optionally one or more carbons of $(CH_2)_x$ and/or $(CH_2)_y$ may form part of a 3 to 7 membered spirocyclic ring;
$R_1$ and $R_2$ are the same or different and are independently selected from alkyl, arylalkyl, cycloalkyl, alkenyl, cycloalkenyl, aryl, heteroaryl or cycloheteroalkyl;
$R_3$ is H or lower alkyl;
$R_4$ is H, halogen, $CF_3$, hydroxy, alkyl, alkoxy, carboxyl, carboxylalkyl-, aminoalkyl, amino, alkanoylamino, aroylamino, cyano, alkoxyCON($R_{10}$)—, $R_{11}R_{12}$NCO—, $R_{11}R_{12}$NCO_2—, $R_{13}SO_2$N($R_{10}$)—, $R_{11}R_{12}$NSO_2N($R_{10}$)—, $R_{13}OCO_2$— or $R_{13}OCO$—;

$R_{13}$ is alkyl, arylalkyl, cycloalkyl, alkenyl, cycloalkenyl, aryl, heteroaryl or cycloheteroalkyl, $R_{11}$ and $R_{12}$, and $R_{10}$ are the same or different and are independently selected from H, alkyl, arylalkyl, cycloalkyl, alkenyl, cycloalkenyl, aryl, heteroaryl or cycloheteroalkyl; or $R_{11}$ and $R_{12}$ may be taken together with the nitrogen to which they are attached to form a stable 3 to 8 membered heterocyclic ring which, where applicable, includes a total of 1 to 3 heteroatoms in the ring, which heteroatoms may be N, O or S;

$R_7$ is H or lower alkyl; and

represents a single bond or a double bond (which may be cis or trans);

and including pharmaceutically acceptable salts thereof when $R_3$ is H, esters thereof, prodrug esters thereof, and all stereoisomers thereof.

Preferably, the Z group will be in form of a free acid, a physiologically acceptable and hydrolyzable ester or δ lactone thereof, or an alkali metal salt, alkaline earth metal salt or an amino acid salt.

Preferred are compounds of formula I of the invention wherein $R_1$ and $R_2$ are independently selected from alkyl, cycloalkyl and aryl;

$R_4$ is H, alkyl, or halogen;

x is 2 or 3;

y is o; and n is o.

More preferred are compounds of formula I of the invention wherein $R_1$ is aryl (especially substituted aryl as defined hereinafter);

$R_2$ is alkyl or cycloalkyl;

$R_4$ is H;

x is 3;

y is o;

n is o; and

is a double bond.

Still more preferred are compounds of formula I of the invention wherein $R_1$ is substituted aryl, preferably 4-fluorophenyl, 4-fluoro-3-methylphenyl or 3,5-dimethylphenyl;

$R_2$ is alkyl or cycloalkyl, preferably isopropyl, t-butyl or cyclopropyl;

$R_4$ is H;

x is 3;

y is o;

n is o;

is a double bond, preferably "trans"; and

Z is

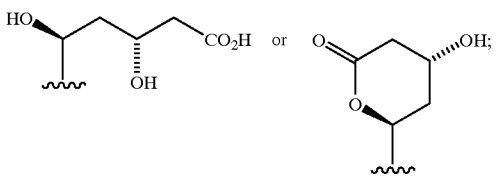

or an alkali metal salt thereof, alkaline earth metal salt or an amino acid salt.

Most preferred compounds of formula I of the invention will have the structure IA: IA

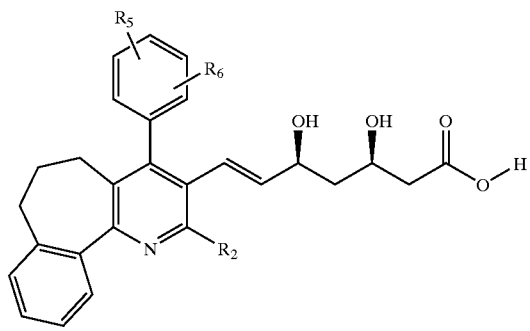

or an alkali or alkaline earth metal (such as Na, K or Ca) salt thereof, or amino acid salt (such as arginine), wherein $R_5$ and $R_6$ are the same or different and independently selected from H, halogen and/or alkyl (preferably 4-fluoro, 4-fluoro-3-methyl or 3,5-dimethyl); and $R_2$ is alkyl or cycloalkyl, preferably isopropyl, t-butyl or cyclopropyl.

In another aspect, the present invention provides pharmaceutical compositions, useful as hypolipidemic or hypocholesterolemic agents, or hypotriglyceridemic agents, or anti-Alzheimer's agents, or anti-osteoporosis agents as well as other uses as described herein, comprising a hypolipidemic or hypocholesterolemic or hypotriglyceridemic or anti-Alzheimer's disease or anti-osteoporosis amount, or other therapeutically effective amount (depending upon use) of a compound of formula I in accordance with this invention, in combination with a pharmaceutically acceptable carrier.

In another aspect, the present invention provides a method of inhibiting cholesterol biosynthesis or lowering blood serum cholesterol levels and/or modulating blood serum cholesterol levels such as lowering LDL cholesterol and/or increasing HDL cholesterol, or treating dyslipidemia, mixed dyslipidemia, hyperlipidemia, hypercholesterolemia, hypo α-lipoproteinemia, LDL Pattern B, LDL Pattern A, hyperlipoproteinemia or hypertriglyceridemia, and other aberrations of apolipoprotein B metabolism, or reducing levels of Lp(a), or treating or preventing other cholesterol-related diseases, or treating or preventing or reversing progression of atherosclerosis, or preventing or treating Alzheimer's disease, or preventing or treating osteoporosis and/or osteopenia, or reducing inflammatory markers such as C-reactive protein, or preventing or treating low grade vascular inflammation, or preventing or treating stroke, or preventing or treating dementia, or preventing or treating coronary heart disease (including primary and secondary prevention of myocardial infarction), or preventing or treating stable and unstable angina, or primary prevention of coronary events, or secondary prevention of cardiovascular events, or preventing or treating peripheral vascular disease, preventing or treating peripheral arterial disease, or preventing or treating acute vascular syndromes, or preventing or reducing the risk of undergoing myocardial revascularization procedures, or preventing or treating microvascular diseases such as nephropathy, neuropathy, retinopathy and nephrotic syndrome or preventing or treating hypertension in a patient in need of such treatment by administering a pharmaceutical composition in accordance with the present invention as defined above.

In addition, in accordance with the present invention, a method is provided for preventing or treating diabetes, especially Type 2 diabetes, and related diseases such as insulin resistance, hyperglycemia, hyperinsulinemia, elevated blood levels of fatty acids or glycerol, obesity, Syndrome X, diabetic complications, dysmetabolic syndrome, and related diseases, and sexual dysfunction, wherein a therapeutically effective amount of a compound of structure I is administered to a patient in need of treatment.

In addition, in accordance with the present invention, a method is provided for preventing and treating malignant lesions (such as ductal carcinoma in situ of the breast and lobular carcinoma in situ of the breast), premalignant lesions (such as fibroadenoma of the breast and prostatic intraepithelial neoplasia (PIN), gastrointestinal malignencies, liposarcomas and various other epithelial tumors (including breast, prostate, colon, ovarian, gastric and lung), cancer-induced asthenia (fatigue), irritable bowel syndrome, Crohn's disease, gastric ulceritis, and gallstones, and HIV infection, other infectious diseases, drug-induced lipodystrophy, and proliferative diseases such as psoriasis, wherein a therapeutically effective amount of a compound of structure I is administered to a human patient in need of treatment.

In addition, in accordance with the present invention, a method is provided for improving coagulation homeostasis including reducing plasminogen activating inhibitor (PAI)-1 activity, reducing fibrinogen, and/or reducing platelet aggregation, and/or improving endothelial function, wherein a therapeutically effective amount of a compound of structure I is administered to a patient in need of treatment.

In addition, in accordance with the present invention, a method is provided for treating cholesterol related diseases, diabetes and related diseases, cardiovascular diseases, cerebrovascular diseases as defined above and hereinafter and other diseases as set out above, wherein a therapeutically effective amount of a combination of a compound of structure I and a hypolipidemic agent, and/or lipid modulating agent and/or antidiabetic agent and/or cardiovascular agent, cerebrovascular agent, and/or other type of therapeutic agent, is administered to a patient in need of treatment.

In the above methods of the invention wherein a combination is administered, the compound of structure I will be employed in a weight ratio to the other therapeutic agent (depending upon its mode of operation) within the range from about 0.01:1 to about 500:1, preferably from about 0.5:1 to about 100:1

DETAILED DESCRIPTION OF THE INVENTION

In accordance with the present invention, there is provided compounds useful in inhibiting the enzyme HMG-CoA reductase, which inhibitors are useful as hypocholesterolemic agents, dyslipidemic agents, hypolipidemic agents, hypotriglyceridemic agents, anti-Alzheimer's disease agents, and antiosteoporosis agents as well as other uses as described herein.

The term "coronary events" as employed herein refers to myocardial infarction, myocardial revascularization procedures, angina, cardiovascular death and acute coronary syndrome.

The term "cardiovascular diseases or events" as employed herein refers to atherosclerosis of the coronary arteries, myocardial infarction, including primary MI and secondary MI, recurrent myocardial infarction, angina pectoris (including stable and unstable angina), congestive heart failure, and sudden cardiac death.

The term "cerebrovascular diseases or events" as employed herein refers to cerebral infarction or stroke (caused by vessel blockage or hemmorage), or transient ischemia attack (TIA), syncope, atherosclerosis of the intracranial and/or extracranial arteries, and the like.

The term "cholesterol-related diseases" as employed herein refers to diseases involving elevated levels of LDL cholesterol, diseases involving regulation of LDL receptors, diseases involving reduced levels of HDL cholesterol, dyslipidemia, hyperlipidemia, elevated LDL Pattern B, elevated LDL Pattern A, hypercholesterolemia, hypo α-lipoproteinemia (low HDL cholesterol syndrome), hyperlipoproteinemia, elevated Lp(a) levels, hypertriglyceridemia, other aberrations of apolipoprotein B metabolism, heterozygous familial, presumed familial combined and non-familial (non-FH) forms of primary hypercholesterolemia (including Frederickson Types IIa and IIb), cholesterol ester storage disease, and cholesterol ester transfer protein disease, and related diseases.

The conditions, diseases, and maladies collectively referenced to as "Syndrome X" or Dysmetabolic Syndrome (as detailed in Johanson, *J. Clin. Endocrinol. Metab.*, 1997, 82, 727–734, and other publications) include hyperglycemia and/or prediabetic insulin resistance syndrome, and is characterized by an initial insulin resistant state generating hyperinsulinemia, dyslipidemia, and impaired glucose tolerance, which can progress to Type II diabetes, characterized by hyperglycemia, which can progress to diabetic complications.

The term "diabetes and related diseases" refers to Type II diabetes, Type I diabetes, impaired glucose tolerance, obesity, hyperglycemia, Syndrome X, dysmetabolic syndrome, diabetic complications and hyperinsulinemia.

The conditions, diseases and maladies collectively referred to as "diabetic complications" include retinopathy, neuropathy and nephropathy, and other known complications of diabetes.

The term "other type(s) of therapeutic agents" as employed herein refers to one or more antidiabetic agents (other than compounds of formula I), one or more anti-obesity agents, and/or one or more lipid-lowering agents, one or more lipid modulating agents (including anti-atherosclerosis agents), other types of anti-atherosclerosis agents, and/or one or more antiplatelet agents, one or more agents for treating hypertension, one or more anti-cancer drugs, one or more agents for treating arthritis, one or more anti-osteoporosis agents, one or more agents for treating immunomodulatory diseases.

The term "lipid-modulating" agent as employed herein refers to agents which lower LDL and/or raise HDL and/or lower triglycerides and/or lower total cholesterol and/or other known mechanisms for therapeutically treating lipid disorders.

The term "other types of anti-atherosclerosis agents" as employed herein refers to conventional anti-atherosclerosis agents including lipoxygenase inhibitors, ACAT inhibitors, antioxidants, PPAR agonists, phospholipase inhibitors (including PLA-2 inhibitors), and/or other known anti-atherosclerosis agents.

The terms pharmaceutically acceptable "salt" and "salts" refer to basic salts formed with inorganic and organic bases. Such salts include ammonium salts; alkali metal salts, such as lithium, sodium and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C1–4) alkyl or arylsulfonic acids which are unsubstituted or substituted, for example by halogen, for example methanesulfonic acid or p-toluenesulfonic acid.

The term "spirocyclic ring" as used in reference to $(CH_2)_x$ and/or $(CH_2)_y$ refers to a 3 to 7 membered spirocyclic ring formed from one or more of the carbons in $(CH_2)_x$ and/or one or more carbons in $(CH_2)_y$, together with additional carbons to make up a 3 to 7 membered ring.

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, cycloheteroalkyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

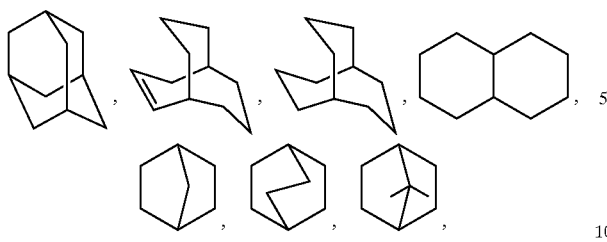

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, heteroaryl, cycloheteroalkyl, amino, alkylamino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio and/or any of the alkyl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted with 1 or 2 substituents as defined above for "alkyl", such as, for example alkyl, halo, hydroxy, alkoxy and/or cycloalkyl.

Where alkenyl groups as defined above and alkynyl groups as defined above, respectively, have single bonds for attachment at two different carbon atoms, they are termed "alkenylene groups" and "alkynylene groups", respectively, and may optionally be substituted with 1 or 2 substituents as defined above for "alkenyl" and "alkynyl".

$(CH_2)_x$ or $(CH_2)_y$ includes alkylene groups as defined herein, which may optionally include 1, 2, or 3 substituents which include alkyl, alkenyl, halogen, aryl, hydroxy, alkoxy, or $C_3$–$C_6$ cycloalkyl.

Examples of $(CH_2)_x$ or $(CH_2)_y$, alkylene groups include —$CH_2$—, —$CH_2CH_2$—,

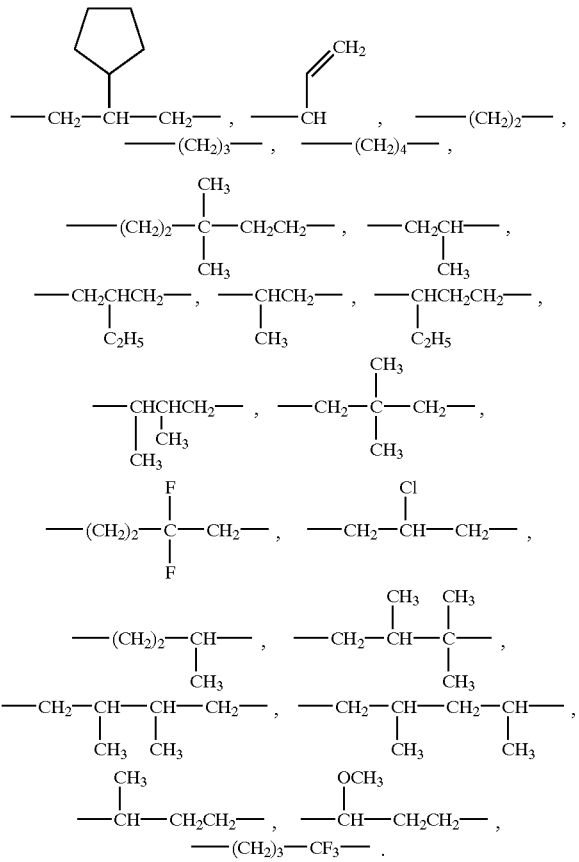

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

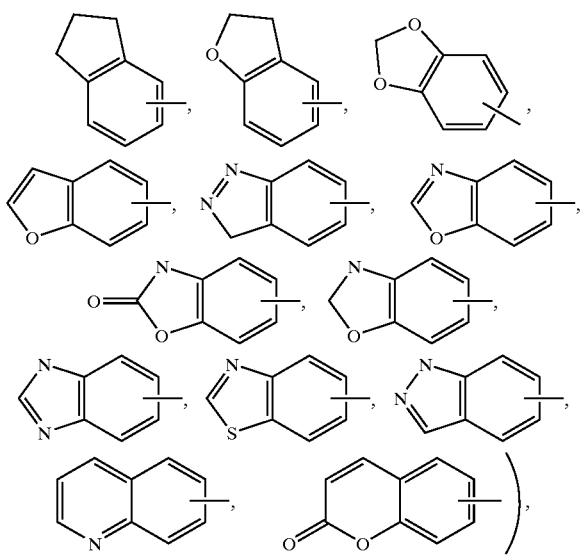

and may be optionally substituted through available carbon atoms with 1, 2, or 3 groups selected from hydrogen, halo, haloalkyl, alkyl, haloalkyl, alkoxy, halophenyl, benzoyloxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, alkanoyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid and/or any of the substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl

group; examples of acyl groups include any of the $R^1$ groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_r$ (where r is 1, 2 or 3), such as

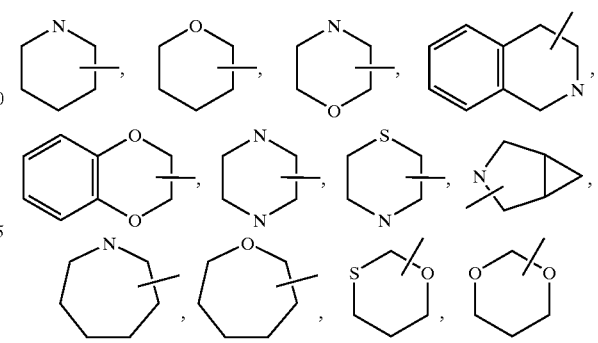

and the like. The above groups may include 1 to 4 substituents such as alkyl, halo, oxo and/or any of the alkyl substituents set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur,and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the substituents set out above for alkyl. Examples of heteroaryl groups include the following:

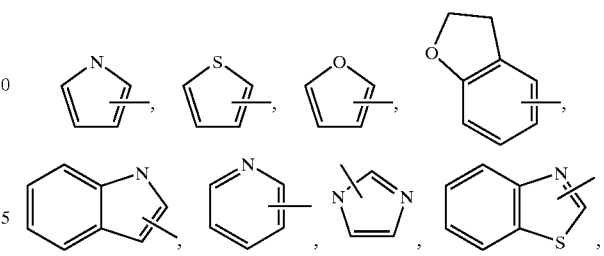

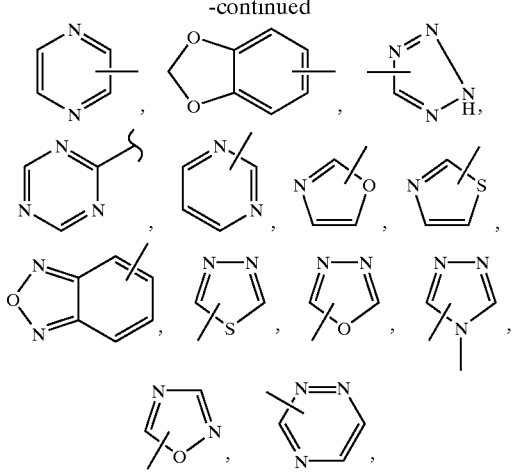

-continued and the like.

The term "cycloheteroalkylalkyl" as used herein alone or as part of another group refers to cycloheteroalkyl groups as defined above linked through a C atom or heteroatom to a $(CH_2)_r$ chain.

The term "heteroarylalkyl" or "heteroarylalkenyl" as used herein alone or as part of another group refers to a heteroaryl group as defined above linked through a C atom or heteroatom to a $-(CH_2)_r-$ chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkoxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like. In addition, prodrug esters which are known in the art for carboxylic and phosphorus acid esters such as methyl, ethyl, benzyl and the like.

Examples of such prodrug esters include:

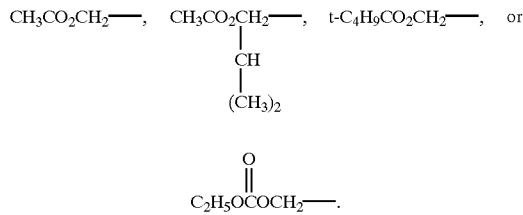

Other examples of suitable prodrug esters include:

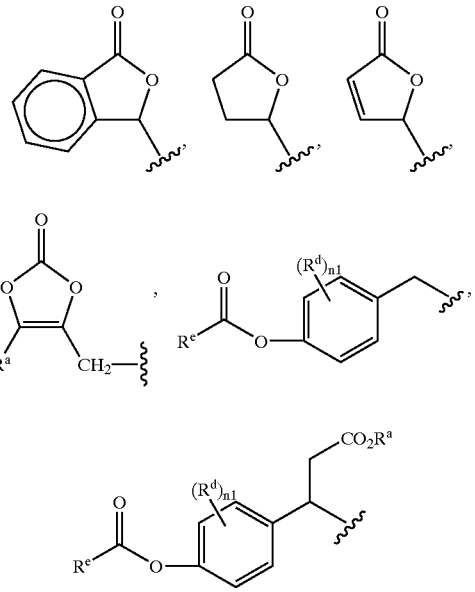

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

Compounds of the invention may be prepared by the following method.

Referring to Reaction Scheme 1, Knovenagel condensation of readily available beta-keto ester 1, where R is lower alkyl, with aldehyde 2 under standard conditions (e.g. HOAc, piperidine, toluene, reflux) affords the corresponding adduct 3. Base induced 1,4-addition of ketone 4 (e.g. LiN(TMS)$_2$ or NaHDMS in THF or EtONa in EtOH) provides the adduct 5, usually as a mixture of diastereomers.

Conversion of the 1,5-diketone 5 to the pyridyl ester 6 may be effected by treatment with an ammonia source (such as NH$_4$OAc) in the presence of an oxidant (such as Cu(OAc)2 or oxygen) in a suitable solvent (such as refluxing HOAc), or by reaction of 5 with hydroxylamine hydrochloride in HOAc with heat. The ester functionality of 6 can be reduced by standard methods (LiAlH$_4$, DIBAL, LiBH$_4$) to give alcohol 7 which can subsequently be converted to the corresponding halide 8 (e.g. PBr$_3$ in CH$_2$Cl$_2$, CBr$_4$/PPh$_3$ in CH$_3$CN, or POCl$_3$). Conversion of halide 8 to the phosphorus compound 9 where W is Ph or alkyl is effected by treatment of 8 with W₂POEt in toluene. Conversion of halide 8 to compound 9 where W is OR (R is lower alkyl) may be effected by the reaction of 8 with HOP(OR)2/base/THF or by Arbuzov reaction with P(OR)₃. Witting reaction between 9 and aldehyde 10 (aldehyde 10 has been previously described in U.S. Pat. No. 5,686,433) may be effected under standard conditions with base (n-BuLi, LiN(TMS)₂, LDA) in an appropriate solvent (THF, Et₂O, toluene, DMPU) to afford the adduct 11. Treatment of 11 under acidic conditions (e.g. TFA, HCl) effects the conversion of 11 to lactone Ia. Saponification of Ia to Ib (where R₃ is alkali metal, or alkaline earth metal) can be effected by treatment of Ia with aqueous base or subsequently acidified to give Ib where R₃ is H. Additionally, Ia can be treated with an alcohol of the type R₃OH under basic conditions to form the corresponding esters of Ib.

As seen in Reaction Scheme 2, the saturated derivatives of compound I (where

is CH₂—CH₂) are obtained by catalytic (Pd/C, Pt/C, Pd(OH)₂) hydrogenation of 11, Ia, or Ib to afford 12, Ic, or Id, respectively. Compound 12 may be converted to Ic and Id following the earlier described methods for the conversion of compound 11 to Ia and Ib.

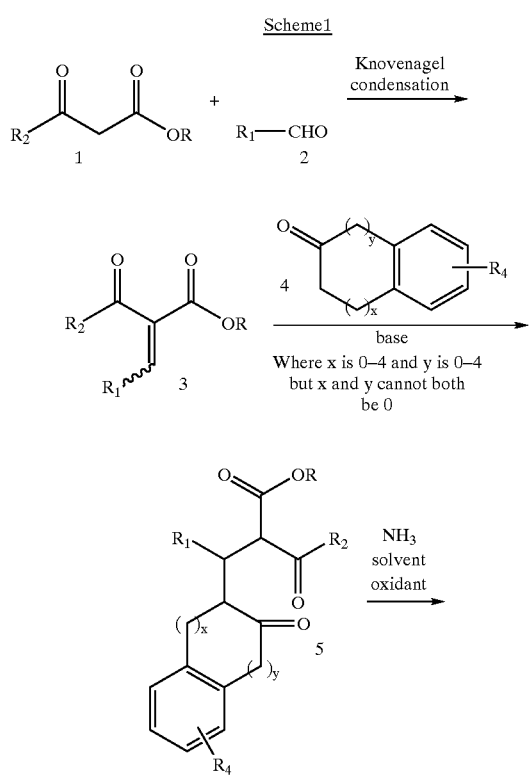

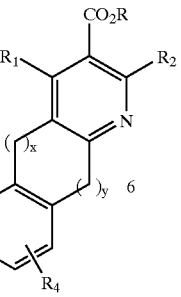

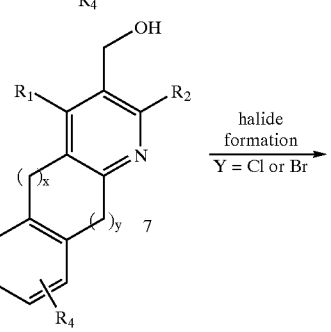

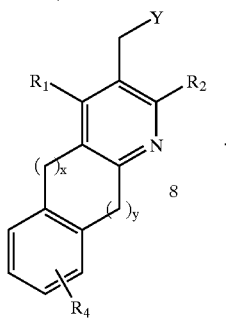

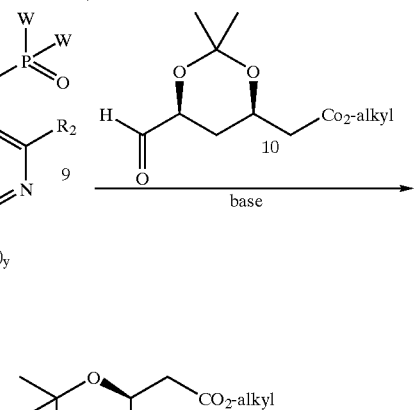

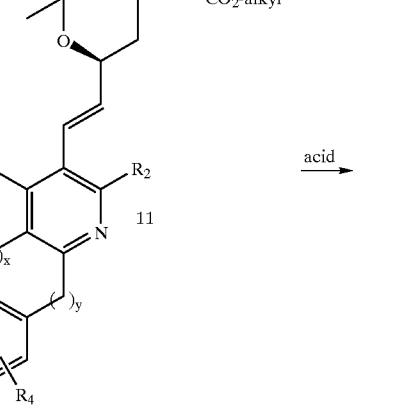

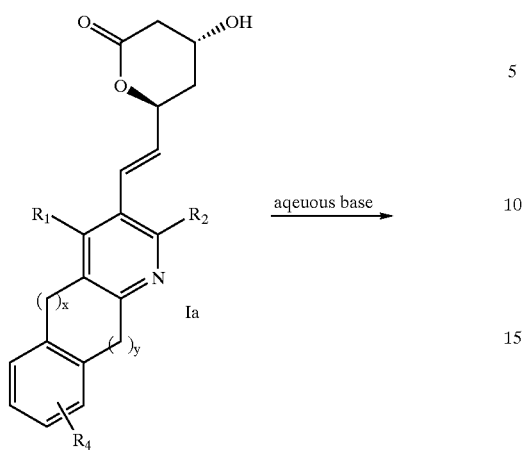
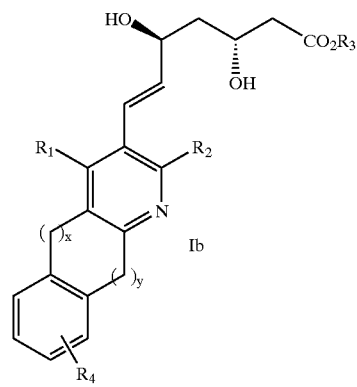
Scheme 2
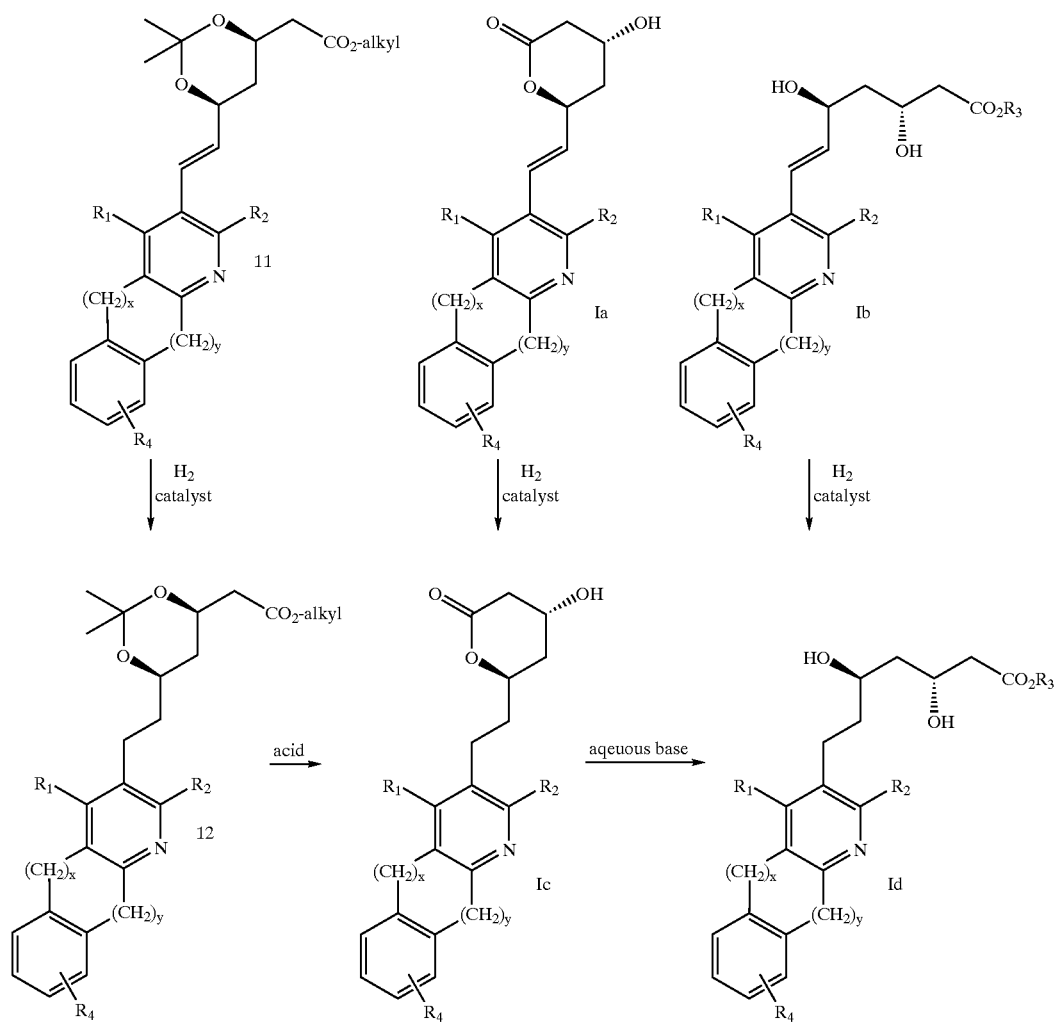

The synthesis of compounds I wherein $$\phantom{x}$$

is CH=CH and n is 1, is described in Scheme 3. Bissilylation of compound $Ib^1$ with a bulky silylchloride (e.g., ClSi(t-butyl)Ph$_2$, ClSi(t-butyl)Me$_2$, ClSiPh$_3$) in the presence of a suitable base (e.g., TEA, imidazole, pyridine) and solvent (e.g., CH$_2$Cl$_2$, THF) provides compound $Ib^2$. Treatment of $Ib^2$ with oxidants such as m-CPBA or CF$_3$CO$_3$H in an appropriate solvent such as CH$_2$Cl$_2$ or HOAc affords N-oxide $Ib^3$. Desilylation of $Ib^3$ (TBAF/HOAc/THF or HF/CH$_3$CN) gives $Ib^4$ which may be saponified to $Ib^5$ using aqueous solutions of a metal hydroxide in an appropriate solvent (e.g., MeOH, dioxane).

Scheme 3

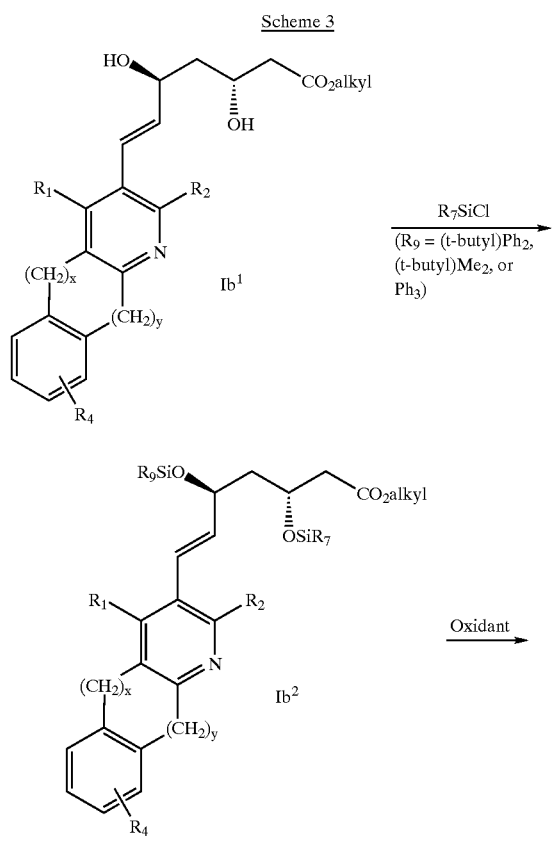

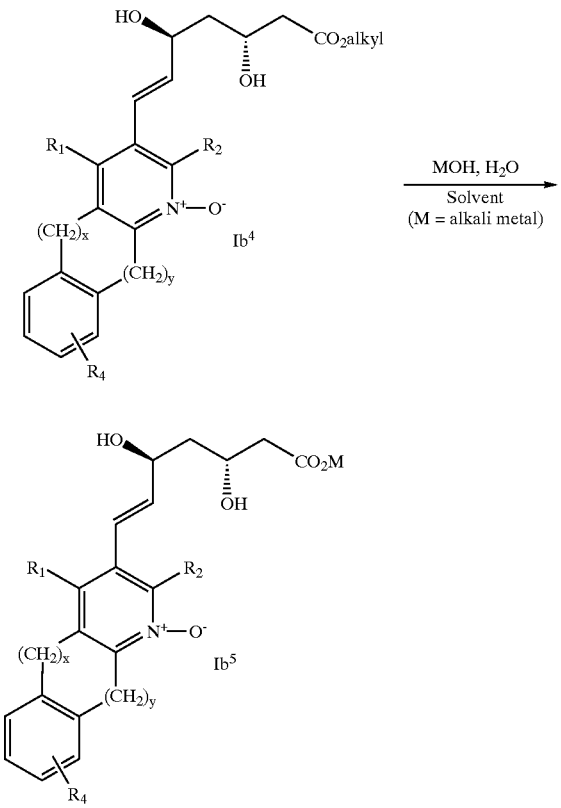

Additionally, compound $Id^1$ may be oxidized and saponified, as described above, to provide compounds I wherein $$\phantom{x}$$

is CH$_2$CH$_2$ and n is 1 (e.g., compounds $Id^2$ and $ID^3$) as shown in Scheme 4.

Scheme 4

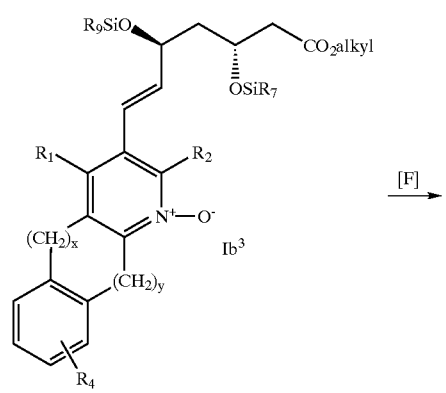

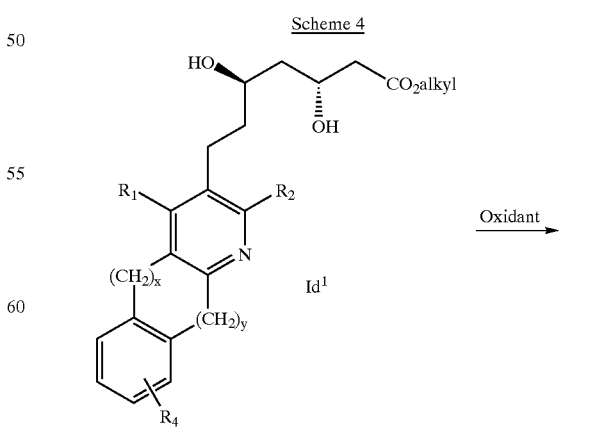

21
-continued

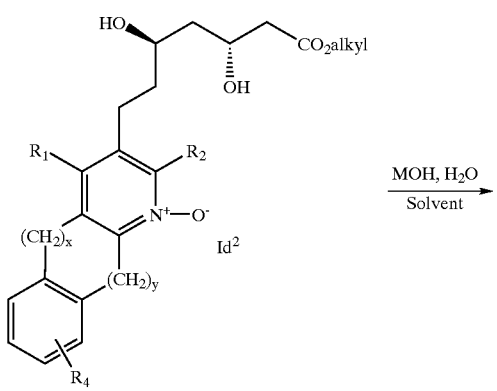

Id²

MOH, H₂O / Solvent →

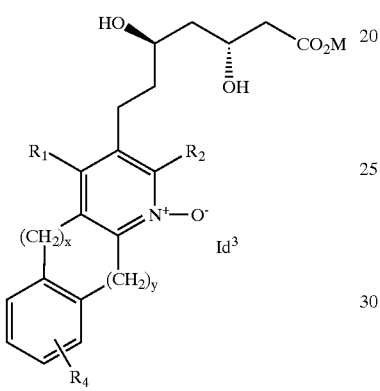

Id³

Referring to Scheme 5, the arginine salt of the compounds of formula I of the invention may be prepared by treating alkali metal salt (preferably sodium) Ib with acid (TFA, HCl) to form the acid Ib⁶ which is treated with arginine in the presence of suitable solvents such as ethyl alcohol and H₂O, ethyl acetate, acetonitrile and the like, to form arginine salt Ib⁷.

Scheme 5

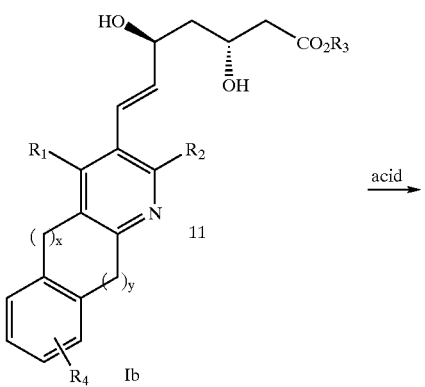

Ib acid →

22
-continued

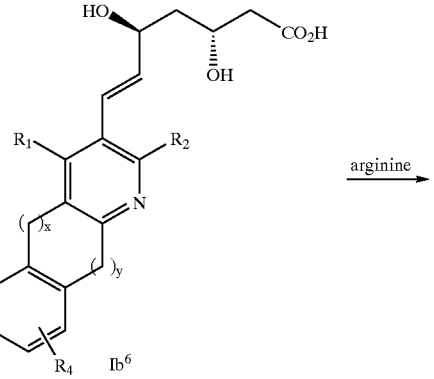

Ib⁶ arginine →

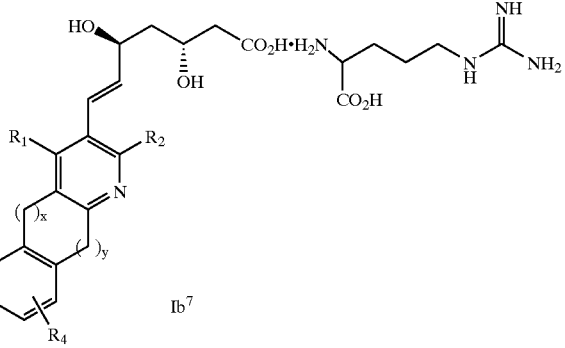

Ib⁷

Scheme 6 depicts a preferred method for preparing the HMG CoA reductase inhibitor of formula I of the invention using the Julia-Kocienski olefination reaction employing 4-pyridyl carboxylaldehyde (18) and chiral sulfone (16). The desired trans intermediate (19) is isolated in high yield and optical purity which is converted to the final product of the invention. As will be seen, the chiral sulfone (16), a key intermediate in the Julia-Kocienski step, is prepared in three steps starting from the commercially available Kaneka alcohol (12) via triflate (13) and sulfide intermediate (15).

Referring to Scheme 6, treatment of commercially available chiral alcohol (12) with triflic anhydride and triethylamine in dichloromethane at low temperature (for example 0 to −30° C.) affords triflate (13). Other pyridine or amine bases may be employed. Triflate (13) (without being isolated) is carried onto the next step without further purification. A methylene chloride solution of triflate (13) is treated with 1-phenyl-1H-tetrazole-5-thiol (14) to provide the chiral sulfide (15) which is oxidized with hydrogen peroxide in the presence of catalytic ammonium heptamolybdate tetrahydrate to give crystalline sulfone (16). Other oxidant, such as m-chloro-p-benzoic acid (mCPBA) may be employed.

Addition of LiHMDS or NaHMDS to a mixture of sulfone (16) and pyridine carboxylaldehyde (18) in THF at low temperature (−78 to −35° C.) provides trans olefin (19) in high diastereoselectivity (>99%).

The pyridine aldehyde (18) is obtained as a crystalline solid form the corresponding ester (17). Reduction of ester (17) with Red-Al followed by oxidation with Tempo (2,2,6,6-tetramethyl-1-piperidinyloxy) gives aldehyde (18) in high yield. The final compound Ib[9] of the invention is prepared in a one pot procedure starting from (19) without isolating any intermediates. Removal of acetonide under acidic condition provides diol (20) which upon further treatment with sodium hydroxide gives the sodium salt of the acid (21). Subsequent treatment of 21 with acid followed by the addition of arginine produces crystalline arginine salt of the invention Ib[9].

Scheme 6

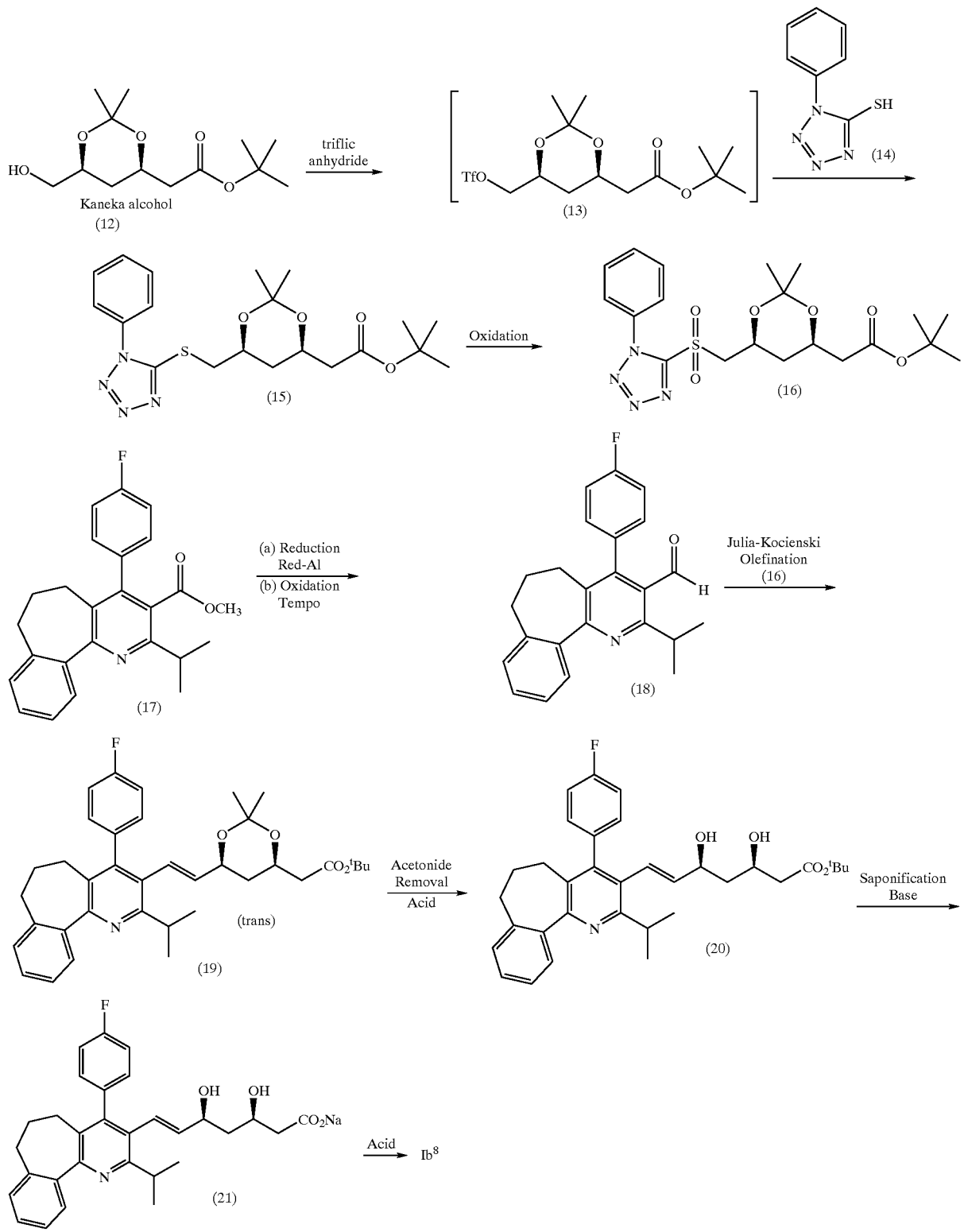

-continued

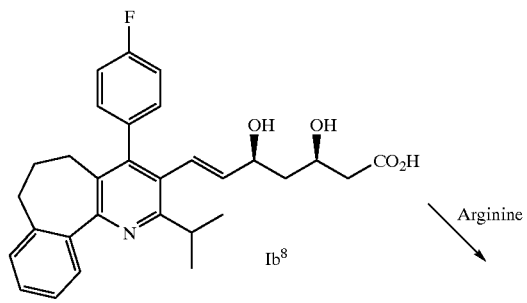
Ib⁸

Arginine ↓

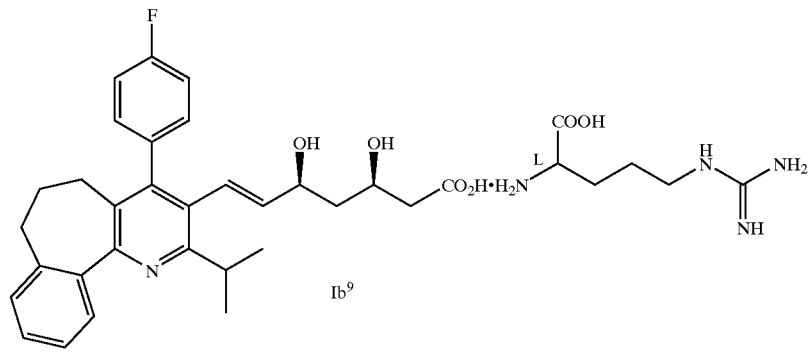
Ib⁹

In addition, in accordance with the present invention, intermediates 6, 7, 8, 9, 11 and 12 are novel compounds and form part of the present invention. These compounds have the general structure

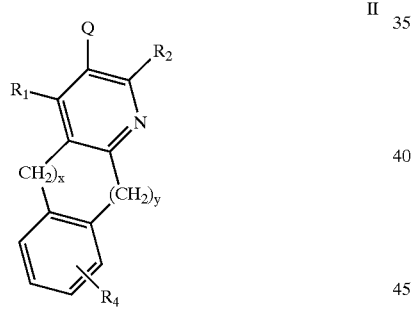
II wherein x, y, $R_1$, $R_2$, $R_4$ are as defined above, Q is:

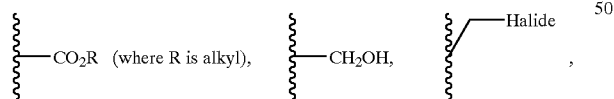

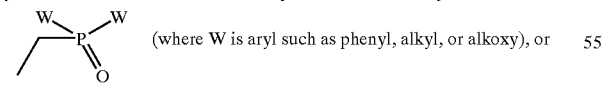
(where W is aryl such as phenyl, alkyl, or alkoxy), or

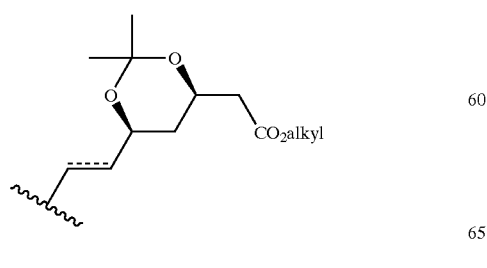

Thus, the intermediates of the invention can have the following structures:

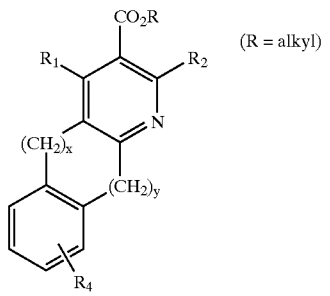
6
(R = alkyl)

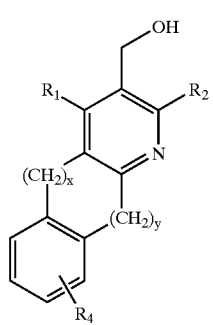
7

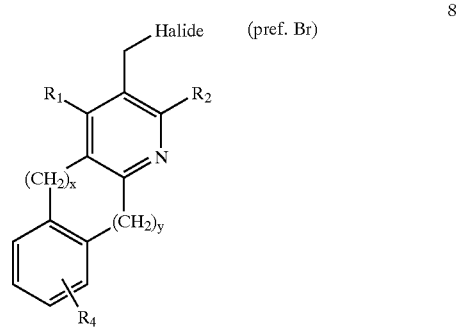
8
(pref. Br)

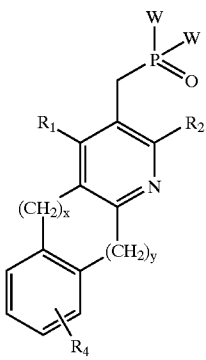

(W = aryl or alkoxy)

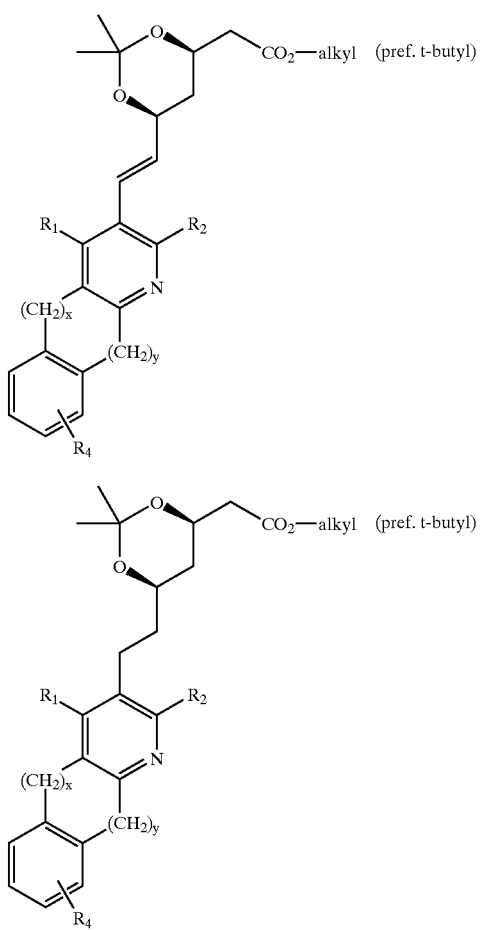

Compounds containing dihydroxy acid HMG-CoA binding domain side chains may be prepared in homochiral form, which is preferred, or may be prepared as racemic mixtures (3S*,5R*) and may later be resolved to obtain the 3S, 5R isomer.

The compounds of the invention are inhibitors of 3-hydroxy-3-methyl-glutaryl coenzyme A (HMG-CoA) reductase and thus are useful in inhibiting cholesterol biosynthesis and/or in lowering triglycerides, in a manner similar to atorvastatin, pravastatin, simvastatin, lovastatin, cerivastatin, visastatin (or rosuvastatin) (Astra Zeneca ZD4522), fluvastatin, itavastatin (or pitavastatin) and the like.

A further aspect of the present invention is a pharmaceutical composition containing at least one of the compounds of formula I of the present invention in association with a pharmaceutical vehicle or diluent. The pharmaceutical composition can be formulated employing conventional solid or liquid vehicles of diluents and pharmaceutical additives of a type appropriate to the mode of desired administration. The compounds can be administered by an oral route, for example, in the form of tablets, capsules, granules or powders, or they can be administered by a parenteral route in the form of injectable preparations. Such dosage forms contain from 0.1 to 1500 mg of active compound per dosage, for use in the treatment. The dose to be administered depends on the unitary dose, the symptoms, and the age and the body weight of the patient.

The compounds of the present invention can be administered in a similar manner as known compounds suggested for use in inhibiting cholesterol biosynthesis, such as pravastatin, lovastatin, simvastatin, visastatin (or rosuvastatin), atorvastatin, cerivastatin, fluvastatin, itavastatin (or pitavastatin), and the like, in mammalian species such as humans, dogs, cats and the like. Thus, the compounds of the invention may be administered in an amount from about 0.1 to 500 mg in a single dose or in the form of individual doses from 1 to 4 times per day, preferably 0.2 to 100 mg daily or in sustained release form.

The HMG CoA reductase inhibitors of formula I may be employed in combination with all therapeutic agents which are useful in combination with HMG CoA reductase inhibitors.

Thus, where desired, the compounds of structure I may be used in combination with one or more hypolipidemic agents or lipid-lowering agents, or lipid agents, or lipid modulating agents, and/or one or more other types of therapeutic agents including antidiabetic agents, anti-obesity agents, antihypertensive agents, platelet aggregation inhibitors, anti-Alzheimer's agents, anti-dementia agents, anti-osteoporosis agents, and/or hormone replacement therapeutic agents, and/or other therapeutic agents, and/or other cardiovascular agents (including anti-anginal agents, anti-arrhythmic agents, anti-atherosclerosis agents, anti-inflammatory agents, anti-platelet agents, anti-heart failure agents), anti-cancer agents, anti-infective agents, hormone replacement agents, growth hormone secretagogues, selective androgen receptor modulators, and/or other therapeutic agents which may be administered orally in the same dosage form or in a separate oral dosage form, or by injection.

The hypolipidemic agent or lipid-lowering agent or other lipid agent or lipid modulating agent which may be optionally employed in combination with the compounds of formula I of the invention may include 1, 2, 3 or more MTP inhibitors, HMG CoA reductase inhibitors, squalene synthetase inhibitors, PPAR α agonists, PPAR dual α/γ agonists, PPAR δ agonists, fibric acid derivatives, ACAT inhibitors, lipoxygenase inhibitors, cholesterol absorption inhibitors, ileal $Na^+$/bile acid cotransporter inhibitors, upregulators of LDL receptor activity, cholesteryl ester transfer protein inhibitors, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875, 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and 5,760,246.

The most preferred MTP inhibitor is 9-[4-[4-[[2-(2,2,2-Trifluoroethoxy)benzoyl]amino]-1-piperidinyl]butyl]-N-(2,2,2-trifluoroethyl)-9H-fluorene-9-carboxamide

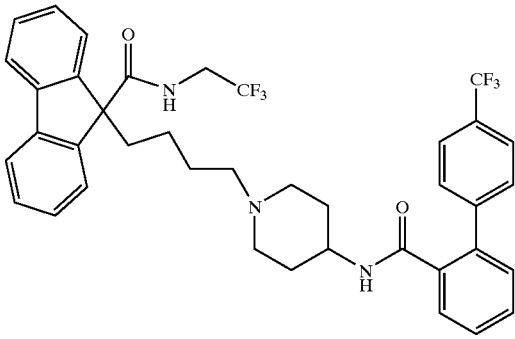

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl) phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphosphoryl-choline (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137 (1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 (ezetimibe) as well as those disclosed in Atherosclerosis 115, 45–63 (1995) and J. Med. Chem. 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in Drugs of the Future, 24, 425–430 (1999).

The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201;

a beta-lactam cholesterol absorption inhibitor such as disclosed in EP 675714;

an HDL upregulator such as an LXR agonist, a PPAR α-agonist and/or an FXR agonist;

an α-glucosidase inhibitor, an aldose reductase inhibitor and/or an LDL catabolism promoter such as disclosed in EP 1022272;

a sodium-proton exchange inhibitor such as disclosed in DE 19622222;

an LDL-receptor inducer or a steroidal glycoside such as disclosed in U.S. Pat. No. 5,698,527 and GB 2304106;

an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E;

isoniazid as disclosed in WO 97/35576;

a cholesterol absorption inhibitor, an HMG-CoA synthase inhibitor, or a lanosterol demethylase inhibitor as disclosed in WO 97/48701;

a PPAR δ agonist for treating dyslipidemia;

or a sterol regulating element binding protein-I (SREBP-1) as disclosed in WO 2000/050574, for example, a sphingolipid, such as ceramide, or neutral sphingomyelenase (N-SMase) or fragment thereof.

Preferred hypolipidemic agents are pravastatin, lovastatin, simvastatin, atorvastatin, fluvastatin, cerivastatin, pitavastatin and rosuvastatin, as well as niacin and/or cholestagel.

The above-mentioned U.S. patents are incorporated herein by reference. The amounts and dosages employed will be as indicated in the Physician's Desk Reference and/or in the patents set out above or as otherwise known in the art.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent or other lipid agent or lipid modulating agent will be as disclosed in the various patents and applications discussed above.

The dosages and formulations for the other hypolipidemic agent or other lipid agent or lipid modulating agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The anti-atherosclerotic agent includes a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties," Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The antidiabetic agent which may be optionally employed in combination with the HMG-CoA reductase inhibitor of formula I may be 1, 2, 3 or more antidiabetic agents or antihyperglycemic agents including insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, aP2 inhibitors, PPAR α/γ dual agonists, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.05:1 to about 10:1.

The sulfonyl urea and PPAR γ agonists in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) or mimetic such as GLP-1(1–36) amide, GLP-1(7–36) amide, GLP-1(7–37) (as disclosed in U.S. Pat. No. 5,614,492 to Habener, the disclosure of which is incorporated herein by reference), as well as AC2993 (Amylen) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the PPAR anti-diabetic agent may be employed in amounts within the range from about 0.01 to about 2000 mg/day which may be administered in single or divided doses one to four times per day.

Where present insulin and other anti-diabetic agents as set out above may be employed in formulations, amounts and dosing as indicated by the Physician's Desk Reference.

Where present GLP-1peptides or mimetics may be administered in oral buccal formulations, by nasal administration or parenterally as described in U.S. Pat. Nos. 5,346,701 (TheraTech), 5,614,492 and 5,631,224 which are incorporated herein by reference.

The antidiabetic agent or other lipid agent may also be a PPAR modulator such as a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998), and in U.S. application Ser. No. 09/664,598, filed Sep. 18, 2000, (attorney file LA29) the disclosure of which is incorporated herein by reference, employing dosages as set out therein, which compounds designated as preferred are preferred for use herein.

The antidiabetic agent may be an SGLT2 inhibitor such as disclosed in U.S. application Ser. No. 09/679,027, filed Oct. 4, 2000 (attorney file LA49), employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000 (attorney file LA27), employing dosages as set out herein. Preferred are the compounds designated as preferred in the above application.

The antidiabetic agent may be a DP4 inhibitor such as disclosed in application Ser. No. 09/788,173, filed Feb. 16, 2001 (attorney file LA50), WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597–11603, 1999, TSL-225 (tryptophyl-1,2,3,4-tetrahydro-isoquinoline-3-carboxylic acid (disclosed by Yamada et al, Bioorg. & Med. Chem. Lett. 8 (1998) 1537–1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996) employing dosages as set out in the above references.

The meglitinide which may optionally be employed in combination with the compound of formula I of the invention may be repaglinide or Starlix® (Novartis), nateglinide (Novartis) or KAD1229 (PF/Kissei), with repaglinide being preferred.

The antidiabetic compound may be a melanocortin receptor agonist such as a spiropiperidine as disclosed in WO 99/64002.

The HMG CoA reductase inhibitor of formula I will be employed in a weight ratio to the meglitinide, PPAR modulator such as a PPAR γ agonist, PPAR α agonist, PPAR δ agonist or antagonist, PPAR α/γ dual agonist, aP2 inhibitor, DP4 inhibitor or SGLT2 inhibitor or other antidiabetic agent within the range from about 0.01:1 to about 100:1, preferably from about 0.05:1 to about 10:1.

The other type of therapeutic agent which may be optionally employed with the HMG CoA reductase inhibitor of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor beta drug, a PTP-1B inhibitor, an anorectic agent, a PPAR modulator including PPAR γ antagonists, PPAR α agonists, PPAR δ antagonists, a CCKA agonist, a leptin inhibitor such as a leptin receptor activator, a neuropeptide Y antagonist, a melanocortin-4-receptor (MC4R) agonist, a fatty acid oxidation upregulator or inducer (such as Famoxin® Genset).

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The neuropeptide Y antagonists which may be optionally employed in combination with a compound of formula I include those described in WO 0113917 (BMS) or in U.S. Pat. No. 6,218,408 (Synaptic) and in WO 0114376 (Banyu).

The lipase inhibitor which may be optionally employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor beta compound which may be optionally employed in combination with a compound of formula I may be a thyroid receptor ligand as disclosed in WO97/21993 (U. Cal SF), WO99/00353 (KaroBio), GB98/284425 (KaroBio), and U.S. Provisional Application No. 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The CCKA agonists which may be employed herein include Glaxo-SmithKline's GI-181,771 and Sanofi's SR146,131.

The PTP-1B inhibitor which may be an anti-obesity and/or an antidiabetic agent include those disclosed in WO 99/585,521, WO 99/58518, WO 99/58522 and WO 99/61435.

The anti-obesity agent employed may also be Pfizer's P57 or CP-644,673 (licensed from Phytopharm).

The various anti-obesity agents described above may be employed in the same dosage form with the compound of formula I or in different dosage forms, in dosages and regimens as generally known in the art or in the PDR.

The antihypertensive agents which may be employed in combination with the HMG CoA reductase inhibitors of the invention include ACE inhibitors, angiotensin II receptor antagonists, NEP inhibitors such as candoxatril, NEP/ACE inhibitors, as well as calcium channel blockers (such as verapamil and amlodipine besylate), T-channel calcium antagonists (such as mibefradil), β-adrenergic blockers, diuretics, α-adrenergic blockers (such as doxazosin mesylate and terazosin HCl), dual action receptor antagonists (DARA), heart failure drugs such as digoxin, and other types of antihypertensive agents.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79–022 and Curr. Ther. Res. 40:74 (1986); Ru 44570 (Hoechst) disclosed in Arzneimittelforschung 34:1254 (1985), cilazapril (Hoffman-LaRoche) disclosed in J. Cardiovasc. Pharmacol. 9:39 (1987); R 31–2201 (Hoffman-LaRoche) disclosed in FEBS Lett. 165:201 (1984); lisinopril (Merck), indalapril (delapril) disclosed in U.S. Pat. No. 4,385,051; indolapril (Schering) disclosed in J. Cardiovasc. Pharmacol. 5:643, 655 (1983), spirapril (Schering) disclosed in Acta. Pharmacol. Toxicol. 59 (Supp. 5):173 (1986); perindopril (Servier) disclosed in Eur. J. clin. Pharmacol. 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid HCl)disclosed in Pharmacologist 26:243, 266 (1984), WY-44221 (Wyeth) disclosed in J. Med. Chem. 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, 5,552,397, 5,504,080, 5,612,359, 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred are omapatrilat, gemopatrilat ([S[(R*,R*)]-hexahydro-6-[(2-mercapto-1-oxo-3-phenylpropyl)amino]-2,2-dimethyl-7-oxo-1H-azepine-1-acetic acid) and CGS 30440.

The angiotensin II receptor antagonist (also referred to herein as angiotensin II antagonist or AII antagonist) suitable for use herein includes, but is not limited to, irbesartan, losartan, valsartan, candesartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist will be as set out in the latest edition of the Physician's Desk Reference (PDR).

Dual action receptor antagonists (DARA) suitable for use herein include those disclosed in U.S. applications Ser. No. 09/513,779, filed Feb. 25, 2000, and Ser. No. 09/604,322, filed Jun. 26, 2000.

Other examples of preferred antihypertensive agents suitable for use herein include omapatrilat (Vanlev®), gemopatrilat, amlodipine besylate (Norvasc®), prazosin HCl (Minipress®), verapamil, nifedipine, diltiazem, felodipine, nisoldipine, isradipine, nicardipine, beta blockers such as nadolol, atenolol (Tenormin®), sotalol, terazosin, doxazosin, carvedilol, and propranolol, and clonidine HCl (Catapres®).

Diuretics which may be employed in combination with compounds of formula I include hydrochlorothiazide, torasemide, furosemide, spironolactone, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antihypertensive agents, diuretics and antiplatelet drugs may be employed in amounts as indicated in the PDR. Ifetroban may be employed in amounts as set out in U.S. Pat. No. 5,100,889.

Anti-Alzheimer's agents or anti-dementia agents suitable for use herein with the HMG CoA reductase inhibitors of the invention include tacrine HCl (Cognex®) and donepezil (Aricept®), as well as γ-secretase inhibitors, β-secretase inhibitors and/or antihypertensive agents. Dosages employed will be as set out in the PDR.

Antiosteoporosis agents suitable for use herein in combination with the HMG CoA reductase inhibitors of the invention include parathyroid hormone or bisphosphonates, such as MK-217 (alendronate) (Fosamax®) as well as Ca receptor agonists and progestin receptor agonists. Dosages employed will be as set out in the PDR.

The hormone replacement therapeutic agents, where present, will be employed in dosages as set out in the latest edition of the PDR. Examples of such agents include selective estrogen receptor modulators (SERMs) such as raloxifen, tamoxifen or lasoxifen.

The HMG CoA reductase compound of the invention may also be employed in combination with a tyrosine kinase inhibitor such as disclosed in WO 2000/053605;

the selective androgen receptor modulator suitable for use herein may be LGD-2226 (Ligand);

the antiarrhythmic agents suitable for use herein include β-blockers as set out herein including sotalol and amioderome, calcium channel blockers as set out herein including verapamil, nifedipine, amlodipine-besylate, and diltiazem, which may also be used in combination with a debrillator device such as a pace maker;

coenzyme Q sub. 10 such as disclosed in U.S. Pat. Nos. 5,316,765, 4,933,165, 4,929,437;

an agent that upregulates type III endothelial cell nitric acid syntase such as disclosed in WO 2000/003746;

a chondroprotective compound such as a polysulfated glycosaminoglycan (PSGAG), glucosamine, chondroitin sulfate (CS), hyaluronic acid (HA), pentosan polysulfate (PPS), doxycycline or minocycline, such as disclosed in EP 970694;

a cyclooxygenase (COX)-2 inhibitor, such as celecoxib (Celebrex® (Searle)) or rofecoxib (Vioxx® (Merck)) or a glycoprotein IIa/IIIb receptor antagonist such as disclosed in WO 99/45913 and tirofiban or abciximab;

a 5-HT reuptake inhibitor such as disclosed in WO 99/44609;

anti-anginal agents such as vasodilators, for example, isosorbide dinitrate, or nitroglycerin;

a growth hormone secretagogue such as disclosed in U.S. applications Ser. No. 09/662,448, filed Sep. 14, 2000, and U.S. Provisional application No. 60/203,335, filed May 11, 2000, and MK-677 (Merck), Pfizer's CP-424391 and Lilly's LY 444,711;

anti-atherosclerosis agents such as ACAT inhibitors and lipoxygenase inhibitors as described herein and phospholipase A-2 inhibitors such as S-3013 and SB-435,495 (which are also anti-inflammatory agents);

anti-infective agents such as quinolones, for example, ciprofloxacin, ofloxacin, and Tequin® (Bristol-Myers Squibb), macrolides such as erythromycin and clarithromycin (Biaxin® (Abbott)), and azithromycin (Zithromax (Pfizer)); or an immunosuppressant (for use in transplantations) such as cyclosporine, mycophenolate mofetil, azathioprine and the like.

As used herein, the phrase "antineoplastic agent" refers to compounds which prevent cancer cells from multiplying. In general, the antineoplastic agents used herein prevent cancer cells from multiplying by: (1) interfering with the cell's ability to replicate DNA, or (2) inducing apoptosis in the cancerous cells.

Examples of antineoplastic agents which are suitable for use in combinations of this invention include, but are not limited to, microtuble-stabilizing agents such as the taxanes, for example, paclitaxel (also known as Taxol®), docetaxel (also known as Taxotere®), 7-O-methylthio-methylpaclitaxel (disclosed in U.S. Pat. No. 5,646,176), 3'-tert-butyl-3'-N-tert-butyloxycarbonyl-4-deacetyl-3'-dephenyl-3'N debenzoyl-4-O-methoxycarbonyl-paclitaxel (disclosed in U.S. Ser. 60/179,965 filed on Feb. 3, 2000, and example 17 herein), C-4 methyl carbonate paclitaxel (disclosed in WO 94/14787), the epothilone, such as epothilone A, epothilone B, epothilone C, epothilone D, desoxyepothilone A, desoxyepothilone B, [1S-[1R*,3R*(E), 7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione (disclosed in WO 99/02514), [1S-[1R*,3R*(E),7R*,10S*, 11R*,12R*,16S*]]-3-[2-[2-(aminomethyl)-4-thiazolyl]-1-methylethenyl]-7,11-di-hydroxy-8,8,10,12,16-pentamethyl-4,17-dioxabicyclo[14.1.0]-heptadecane-5,9-dione (disclosed in U.S. Ser. No. 09/506,481 filed on Feb. 17, 2000, and examples 7 and 8 herein), and derivatives thereof; microtuble-disruptor agents; alkylating agents; anti-metabolites; epidophyllotoxin; an antineoplastic enzyme; a topoisomerase inhibitor; procarbazine; mitoxantrone; platinum coordination complexes; biological response modifiers; growth inhibitors; hormonal/antihormonal therapeutic agents; and haematopoietic growth factors.

Other classes of antineoplastic agents suitable for use in the method of the present invention include, but are not limited to, the anthracycline family of drugs, the vinca drugs, the mitomycins, the bleomycins, the cytotoxic nucleosides, discodermolide, the pteridine family of drugs, diynenes, aromatase inhibitors, and the podophyllotoxins. Particularly useful members of those classes not previously mentioned include, for example, doxorubicin, carminomycin, daunorubicin, aminopterin, methotrexate, methopterin, dichloro-methotrexate, mitomycin C, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, leurosine, and the like. Other useful antineoplastic agents include estramustine, cisplatin, carboplatin, cyclophosphamide, bleomycin, tamoxifen, ifosfamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons, and interleukins.

It will be appreciated that unless otherwise specified the dosage regiment for therapeutic agents used in combination with the compounds of the invention will be as specified in the PDR.

In carrying out the method of the invention for treating hypercholesterolemia, hyperlipidemia, hyperlipoproteinemia, hypertriglyceridemia, or atherosclerosis, and related diseases, or Alzheimer's disease or osteoporosis, or other disclosures as set out hereinbefore, a pharmaceutical composition will be employed containing the compounds of structure I, with or without other cholesterol lowering agents, osteoporosis agents, Alzheimer's agents, antidiabetic agent(s) and/or antihyperlipidemic agent (s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compounds can be administered to mammalian species including humans, monkeys, dogs, etc. by an oral route, for example, in the form of tablets, capsules, beads, granules or powders, or they can be administered by a parenteral route in the form of injectable preparations, or they can be administered intranasally or in transdermal patches. Typical solid formulations will contain from about 0.1 to about 500 mg of a compound of formula I. The dose for adults is preferably between 0.5 and 1,000 mg per day, which can be administered in a single dose or in the form of individual doses from 1–4 times per day and also single dose once weekly (5 to 1000 mg).

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The following abbreviations are employed in the Examples and elsewhere herein:
Ph=phenyl
Bn=benzyl
i-Bu=iso-butyl
Me=methyl
Et ethyl
TMS=trimethylsilyl
FMOC=fluorenylmethoxycarbonyl
Boc=tert-butoxycarbonyl
Cbz=carbobenzyloxy or carbobenzoxy or benzyloxycarbonyl
DIPEA=diisopropyl ethylamine
PTSH=N-phenylthiotetrazole
pph$_3$=triphenylphosphine
NMO=methylmorpholine N-oxide
TPAP=tetrapropylammonium perruthenate
DEAD=diethyl azodicarboxylate
HOAc or AcOH=acetic acid
TFA=trifluoroacetic acid
Et$_2$NH=diethylamine
NMM=N-methyl morpholine
n-BuLi=n-butyllithium
Pd/C=palladium on carbon
PtO$_2$=platinum oxide
MTBE=methyl t-butyl ether
DI water=dionized water
TEA=triethylamine
EDAC=3-ethyl-3'-(dimethylamino)propyl-carbodiimide hydrochloride (or 1-[(3-(dimethyl)amino)propyl])-3-ethylcarbodiimide hydrochloride)
HOBT or HOBT.H$_2$O=1-hydroxybenzotriazole hydrate
HOAT=1-hydroxy-7-azabenzotriazole
PyBOP reagent=benzotriazol-1-yloxy-tripyrrolidino phosphonium hexafluorophosphate
LiN(TMS)$_2$=Libis(trimethylsilyl)amide
DIBAL=diisobutylaluminum hydride
LDA=lithium diisopropylamide
DMPU=1,3-dimethyl-3,4,5,6-tetrahydro-2(1H)-pyrimidinone
AcCN=acetonitrile
LIHMDS=lithium bis(trimethylsilyl)amide
NaHMDS=sodium bis(trimethylsilyl)amide
Red-AL=sodium bis(2-methoxyethoxy)aluminum hydride
mCPBA=m-chloro-p-benzoic acid
min=minute(s)
h or hr=hour(s)

L=liter
mL=milliliter
μL=microliter
g=gram(s)
mg=milligram(s)
mol=moles
mmol=millimole(s)
meq=milliequivalent
RT, rt=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point
Bp=boiling point The following Examples represent preferred embodiments of the invention. Unless otherwise indicated, all temperatures are in degrees Centigrade.

EXAMPLE 1

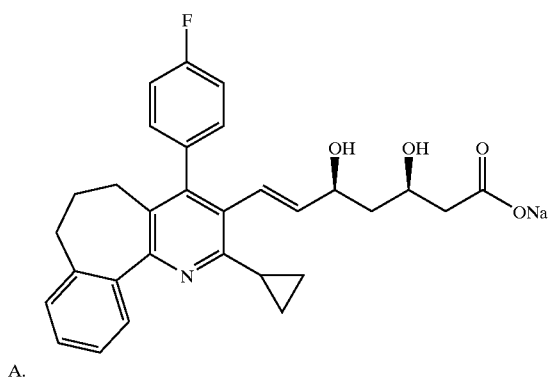

A.

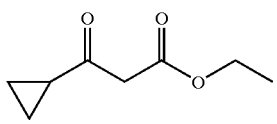

To a slurry of NaH (19.20 g, 480 mmol) and diethyl carbonate (80 mL) in a 3-neck 1 L round bottom flask at room temperature was added a solution of cyclopropyl methylketone (23.5 mL, 238 mmol) in Et$_2$O (30 mL). Approximately 10% of the solution was added, and then 0.25 mL of EtOH was added to the reaction slurry. Addition of the remaining ketone solution continued with light gas evolution. After addition of all of the ketone solution, the reaction became quite exothermic with vigorous H$_2$evolution. The reaction mixture was cooled periodically with an ice-bath to keep the temperature around 35° C. to 50° C. After one hour, gas evolution had ceased and the reaction mixture was stirred at room temperature for 2 h. The reaction mixture was cooled in an ice-bath, diluted with Et$_2$O (200 mL), and treated with 1 N HCl with some ice to adjust to around pH 3. The reaction mixture was extracted with Et$_2$O (3×150 mL) The Et$_2$O extracts were combined, washed with saturated aqueous NaHCO$_3$ (200 mL), H$_2$O (200 mL) and brine (200 mL), and dried (Na$_2$SO$_4$), filtered and concentrated under reduced pressure to give a yellow oil. The oil was distilled under vacuum to give the title compound as a colorless oil, 28.5 g, 77%. B.p.=94–96° C./8 mmHg.

B.

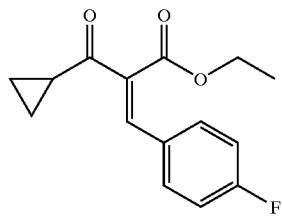

To a stirred solution of Part A compound (28.24 g, 181 mmol) in benzene (128 mL) was added 4-fluorobenzaldehyde (19.4 mL, 181 mmol), HOAc (0.31 mL, 5.4 mmol) and piperidine (1.8 mL, 18.2 mL). The reaction mixture was heated at reflux and azeotrope was collected with a Dean-Stark trap. After 16 h, the reaction was cooled to room temperature, diluted with Et$_2$O (250 mL), washed with aqueous 0.5 N HCl, saturated aqueous NaHCO$_3$, H$_2$O and brine, and then dried (Na$_2$SO$_4$), filtered and concentrated under reduced pressure. Purification by flash chromatography (1:10 EtOAc/hexane) gave the title compound as a light yellow oil, 29 g, 61% yield.

C.

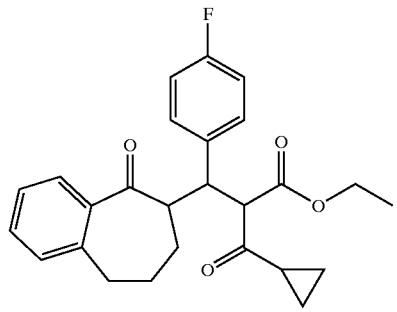

To a solution of 1-benzosuberone (7.35 g, 45.9 mmol) in THF (3 mL) at −78° C. under N$_2$ was added a solution of lithium bis(trimethylsilyl)amide (1 M in THF, 40.5 mL, 40.5 mmol). The reaction mixture was stirred at −78° C. for 1 h, then a solution of Part B compound (7.07 g, 26.95 mmol) in THF (3 mL) was added dropwise. The reaction mixture was stirred at −78° C. for 1 h, then at 0° C. for 30 min. The reaction mixture was quenched with HOAc (8 mL) and poured into saturated aqueous NH$_4$Cl (250 mL), then extracted with Et$_2$O (3×60 mL). The combined Et$_2$O extracts were washed with H$_2$O and brine, then dried (Na$_2$SO$_4$), filtered and concentrated in vacuo to give the title compound as a light yellow oil. The resulting crude product was used in the next step without further purification.

D.

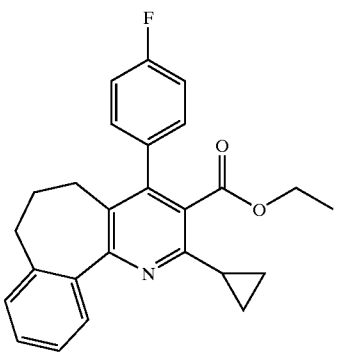

To a stirred solution of crude Part C compound (26.9 mmol) in HOAc (128 mL) was added ammonium acetate (9.14 g, 118.6 mmol) and copper (II) acetate monohydrate (19.7 g, 99.7 mmol). The reaction mixture was heated at reflux under argon overnight. After cooling to room temperature, the reaction mixture was poured into a mixture of NH$_4$OH (150 mL) and ice (~300 g), then extracted with Et$_2$O (3×100 mL). The combined Et$_2$O extracts were washed with H$_2$O and brine, then dried (Na$_2$SO$_4$), filtered and concentrated in vacuo. Purification by flash chromatography (2:20:80-EtOAc/CH$_2$Cl$_2$/hexane) gave the title compound as a white foam, 7.7 g, 71% yield (from Part B compound).

E.

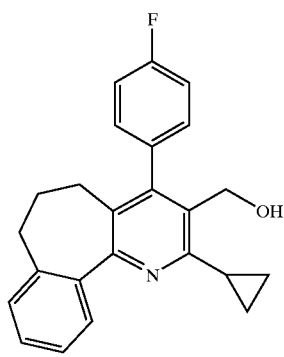

To a stirred solution of Part D compound (7.7 g, 19.2 mmol) in THF (30 mL) at 0° C. under argon was added a solution of lithium aluminum hydride (1 M in THF, 60 mL, 60 mmol) at a rate to maintain the temperature below 10° C. After addition, the reaction mixture was stirred at room temperature for 1.5 h and cooled to 0° C., then carefully quenched with H$_2$O (15 mL), 10% aqueous NaOH (15 mL) and H$_2$O (15 mL). The reaction mixture was stirred at room temperature for 15 minutes and filtered. The solid was washed with Et$_2$O and EtOAc. The combined organic extracts/washings were washed with H$_2$O and brine, then dried (Na$_2$SO$_4$), filtered and concentrated in vacuo. Recrystallization from EtOAc-hexane gave the title compound as a white solid, 5.25 g, 76% yield.

F.

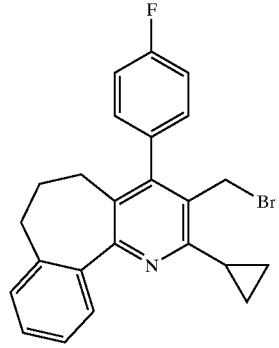

To a slurry of Part E compound (5.2 g, 14.5 mmol) in CH$_2$Cl$_2$ (40 mL) at 0° C. under argon was added a solution of PBr$_3$ (29 mL, 29 mmol) in CH$_2$Cl$_2$ dropwise, maintaining the temperature between 0 to 10° C. After addition, the reaction mixture was stirred at 0° C. for 1 h, then quenched with saturated aqueous NaHCO$_3$ (100 mL) and extracted with EtOAc (3×80 mL). The combined organic extracts were washed with H$_2$O and brine, then dried (Na$_2$SO$_4$), filtered and concentrated in vacuo. Purification by flash chromatography (1:3 CH$_2$Cl$_2$/hexane) gave the title compound as a white powder, 3.85 g, 63% yield.

G.

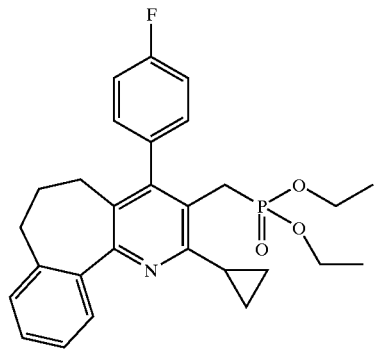

A solution of diethyl phosphite (1.50 g, 10.9 mmol) in THF (10 mL) was cooled to −10° C. under argon and then a solution of sodium bis (trimethylsilyl)amide (1 M in THF, 10.7 mL, 10.7 mmol) was added, dropwise. The reaction mixture was stirred at −10° C. for 30 min, and then a solution of Part F compound (3.82 g, 9.05 mmol) in THF (15 mL) was added maintaining temperature around −10 to 0° C. The reaction mixture was stirred at −10° C. for 1 h. The reaction mixture was quenched with saturated aqueous NH$_4$Cl (150 mL), then extracted with EtOAc (3×100 mL). Combined EtOAc extracts were washed with saturated aqueous NH$_4$Cl (150 mL), H$_2$O and brine, then dried (Na$_2$SO$_4$), filtered and concentrated in vacuo. Purification by flash chromatography (1:2-EtOAc:hexane) gave the title compound as a white foam, 4.1 g, 94% yield.

H.

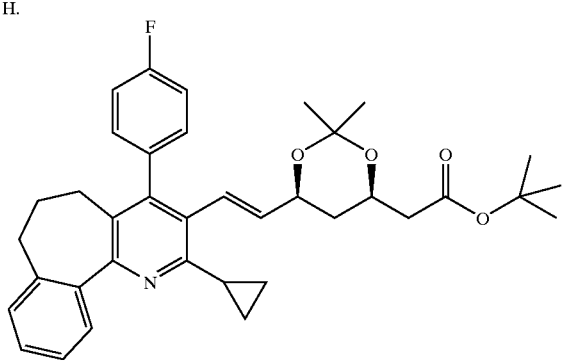

J.

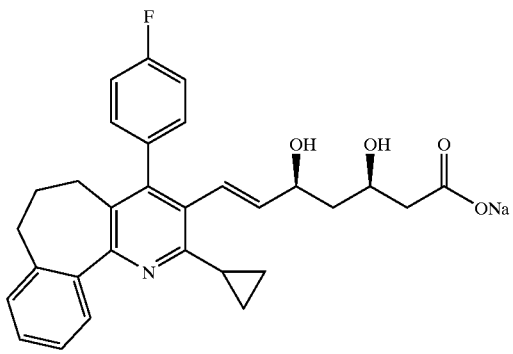

A flame-dried 200 mL round bottom flask was charged with Part G compound (2.062 g, 4.3 mmol) and chased with anhydrous toluene (2×10 mL), then dried on high vacuum and purged with argon. The residue was dissolved in THF (15 mL) and cooled to −78° C. under argon. A solution of nBuLi (2.4 M in hexanes, 1.90 mL, 4.52 mmol) was added dropwise, maintaining the temperature around −78 to −74° C. A solution of the Example 2 Part G aldehyde compound (1.332 g, 5.16 mmole) in THF (10 mL) was added dropwise. The reaction mixture was stirred at −78° C. for 40 min, at −10° C. for 1 h, and at room temperature for 1 h. The reaction mixture was quenched with saturated aqueous $NH_4Cl$ (100 mL), then extracted with EtOAc (2×100 mL). Combined EtOAc layers were washed with $H_2O$ and brine, then dried ($Na_2SO_4$), filtered and concentrated in vacuo. Purification by flash chromatography (27:973-EtOAc:$CH_2Cl_2$) gave the title compound as a white foam, 804 mg, 34% yield.

I.

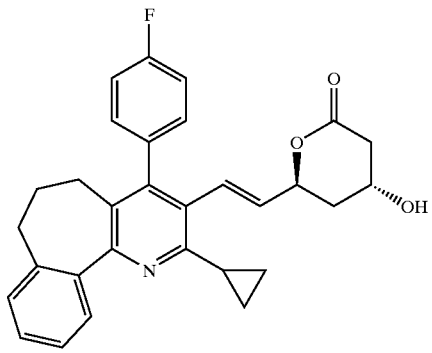

To a solution of part H compound (804 mg, 1.38 mmol) in $CH_2Cl_2$ (18 mL) at 0° C. under argon was added trifluoroacetic acid (1.59 mL, 20.7 mmol). The reaction mixture was stirred at room temperature for 5 h, diluted with EtOAc (100 mL) and washed with saturated aqueous $NaHCO_3$ (60 mL×2), $H_2O$ and brine, then dried ($Na_2SO_4$), filtered and concentrated in vacuo. Purification by flash chromatography (45:55-EtOAc:hexane) gave the title compound as a white foam, 540 mg, 83% yield.

To a solution of Part I compound (515 mg, 1.1 mmol) in THF (10 mL) was added iN aqueous NaOH (1.37 mL, 1.37 mmol) and stirred at room temperature for 10 min. The reaction mixture was concentrated in vacuo and purified by SP207 ($Na^+$ form) resin, eluting with 3:7-$H_3CN$:$H_2O$. The desired fractions were pooled and lyophilized to give the title compound as a white powder, 506 mg, 91% yield. LRMS gave the correct molecular ion [$(M-Na^++2H^+)=488$] for the desired compound.

EXAMPLE 1A

Alternate Procedure for Example 1 Part H compound (1).

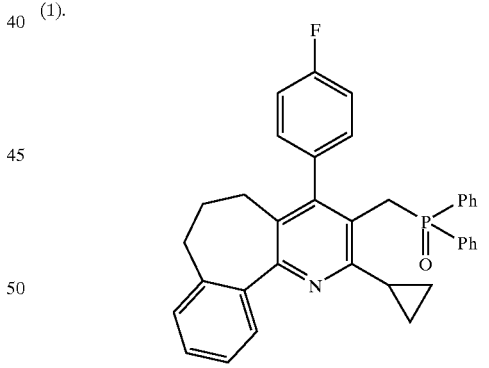

To a stirred solution of Example 1 Part E compound (13.07 g, 31.0 mmol) in toluene (300 mL) was added O-ethyl diphenylphosphinate (8.65 mL, 40.0 mmol) in one portion. The reaction was heated to reflux, using a Dean-Stark trap to remove the ~15 mL of solvent. After 2 h, the solution was cooled and evaporated to nearly remove all of the solvent. The residue was triturated in hexanes (~100 mL), the resulting solids were collected and dried in vacuo at 60° C. to give Part (1) compound as a white solid, 15.25 g, 91% yield, mp 201–203° C.

(2).

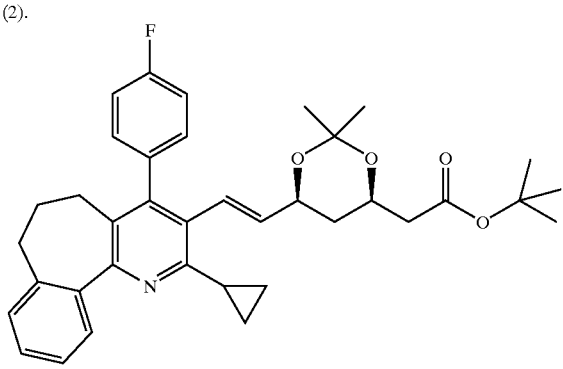

A 1 L 3-necked round bottom flask was flame-dried and then fitted with a mechanical stirrer, an argon-filled balloon, vacuum take-off and a thermocouple. To a stirred slurry of Part (1) compound (7.00 g, 12.9 mmol) in THF (200 mL) at 0° C. was added n-butyllithium solution (5.4 mL, 2.5 M in hexanes, 13.5 mmol) over 20 min. A deep red-orange solution formed. After 30 min, a solution of zinc chloride-N,N,N',N'-tetramethylethylene-diamine complex (dried in vacuo at 60° C. for 2 h, 2.42 g, 13.5 mmol) in THF (100 mL) was added via cannula and stirred 30 min. After 30 min, the resulting solution was cannulated into a solution of Example 2 Part G aldehyde (4.30 g, 16.6 mmol) in THF (20 mL) at room temperature over 20 min. A light orange solution soon formed, followed by a precipitate. After 3 h, the reaction was quenched with brine (50 mL) and water (50 mL) and extracted three times with ethyl acetate (100 mL). The organic extracts were combined, dried (MgSO$_4$) and evaporated. LCMS of the crude material indicated unreacted Part (1) compound and an 89/11 mixture of the desired (E) isomer/undesired (Z) isomer.

The reaction was repeated and the combined crude product (28 g) was purified by flash chromatography on silica gel in two identical batches (12×22 cm column, 1.5 L 1:99 EtOAc/CH$_2$Cl$_2$, 2 L 1:39 EtOAc/CH$_2$Cl$_2$ and then 1.5 L 3:7 EtOAc/hexanes). Partially pure E/Z mixtures were pooled and repurified to give the title Part (2) compound (which is the same as Example 1 Part H compound) (99.2% (E) isomer) as a crystalline solid (after evaporation from toluene), mp 146–147° C., 7.14 g (68% yield, based on recovered Part (1) compound).

EXAMPLE 2

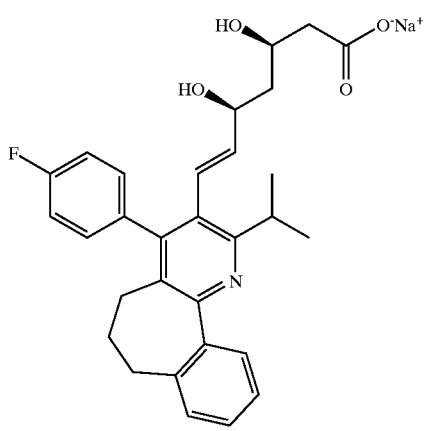

A.

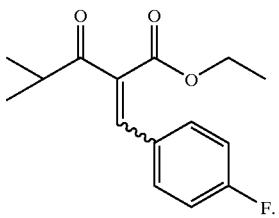

To a solution of 4-fluoro-benzaldehyde (5 g, 40.3 mmol) and ethyl isobutyryl acetate (6.5 mL, 40.3 mmol) in benzene (50 mL) was added piperidine (400 μl, 4.04 mmol), followed by acetic acid (100 μl, 1.66 mmol). The reaction was refluxed for 16 hours and partitioned between aqueous HCl (1N, 20 mL) and ethyl acetate (50 mL×2). The combined organic layers were washed with saturated NaHCO$_3$ (20 mL), brine (10 ml), and dried over sodium sulfate (Na$_2$SO$_4$). The solvent was removed in vacuo. Distillation at 140° C. at 300 mm Hg afford 9.06 g (85% yield) of compound A as a yellow oil. ESI–LC/MS (M+H)$^+$=264.

B.

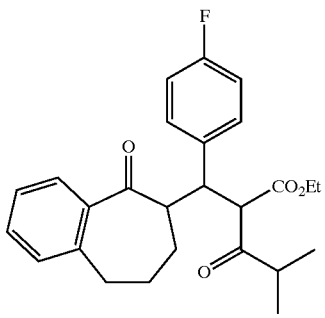

To a 1M lithium hexamethyldisazide solution (50 mL, 50 mmol) at −78° C. under N$_2$ was added a THF (3 mL) solution of benzosuborone (9 g, 56.1 mmol). The reaction temperature was maintained below −75° C. during the addition. The reaction was then stirred at −78° C. for 1 hour and compound A (9 g, 34.1 mmol, in 3 mL THF) was slowly added to the reaction. After the addition was complete, the reaction was stirred for 1 hour at −74° C. then warmed to 0° C. and stirred for 20 minutes. The reaction was quenched with HOAc (9 mL) and poured into saturated ammonium chloride solution (NH$_4$Cl, 20 mL). The aqueous layer was extracted with ethyl ether (100 mL×3). The combined organic layers were washed with water (30 mL) and brine (30 mL), then dried over sodium sulfate (Na$_2$SO$_4$). The solvent was removed in vacuo and stripped with toluene twice to afford crude compound B. The crude compound B was used directly in the next step. ESI–LC/MS (M+H)$^+$=425.

C.

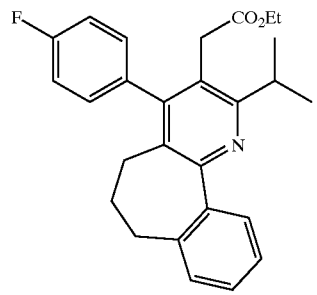

To a solution of the crude compound B (12 g) in aqueous HOAc (100 mL) was added ammonium acetate (9.5 g, 123.2 mmol), followed by cupric acetate monohydrate (20.7 g, 113.9 mmol). The reaction was reflux for 20 hours, cooled to room temperature, then poured into a solution of ammonium hydroxide in ice (1 to 1; v/v). The aqueous layer was extracted with ethyl ether (200 mL×3). The combined organic layers were washed with water (50 mL) and brine (50 mL). Flash chromatography (10% ethyl acetate in hexane) afforded 10.2 g (88% yield) of compound C as white powder. ESI-LC/MS (M+H)$^+$=404; m.p. 138–140° C.

D.

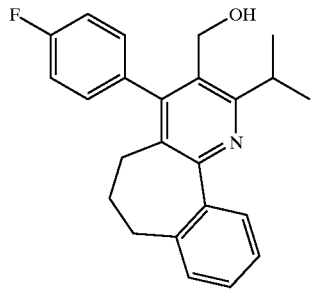

To a solution of compound C (10 g, 24.78 mmol) in anhydrous THF (240 mL) at 0° C. was added 1.0 M lithium aluminum hydride in THF (74 mL, 74 mmol). The reaction was stirred at 0° C. for 1 hour and then warmed to room temperature and stirred for 16 hours. The reaction was then cooled to 0° C. and quenched slowly with ice, then sodium hydroxide (10% NaOH, 20 mL). The mixture was extracted with diethyl ether (50 mL×2) and filtered. The filter cake was then washed with more ethyl ether (10 mL) and ethyl acetate (10 mL). The combined organic layers were washed with water (10 mL) and brine (10 mL), then dried over sodium sulfate (Na$_2$SO$_4$). Flash chromatography (20% ethyl acetate in hexane) afforded 6.5 g (73% yield) of compound D. ESI-LC/MS (M+H)$^+$=362; m.p. 170–171° C.

E.

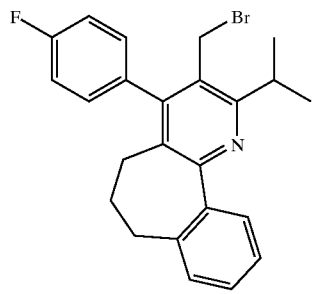

To a solution of compound D (8.5 g, 23.54 mmol) in anhydrous CH$_2$Cl$_2$ (100 mL) at 0° C. was slowly added 1.0 M phosphorous tribromide in CH$_2$Cl$_2$ (47 mL, 47.1 mmol) while maintaining the temperature below 10° C. After the addition was complete, the reaction was stirred at 0° C. for 1 hour and then poured into saturated cold NaHCO$_3$ solution (200 mL) with stirring. The aqueous layer was extracted with CH$_2$Cl$_2$ (50 ml×2) and the combined organic layer was washed with water (10 mL) and brine (10 mL), then dried over sodium sulfate (Na$_2$SO$_4$). Flash chromatography (10% ethyl acetate in hexane) gave 8.6 g (86% yield) of compound E as a white solid. ESI-LC/MS (M+H)$^+$=424; m.p. 157–159° C.

F.

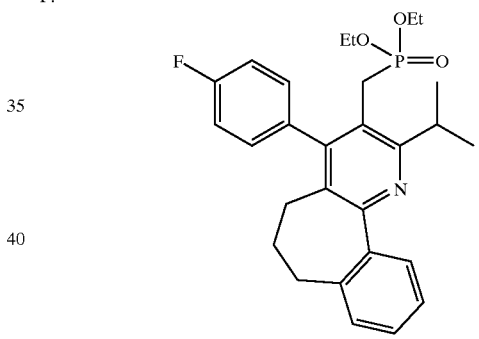

To a solution of diethyl phosphite (785 μL, 6.09 mmol) in anhydrous THF (25 mL) at −10° C. under argon was added a 1.0 M THF solution of sodium hexamethyldisazide (6 mL, 6.09 mmol). The reaction mixture was stirred at −10° C. for 30 minutes. A solution of compound E (2.15 g, 5.08 mmol) in THF was added to the reaction while maintaining the temperature at −10° C. After the addition was complete, the reaction was stirred for 1 hour and quenched with water (20 mL). The aqueous layer was extracted with ethyl acetate (30 mL×2) and the combined organic layers were washed with iN HCl solution (5 mL). The organic solvent was removed in vacuo. Flash chromatography using 20% to 30% ethyl acetate in hexane as eluting afforded 2.29 g (94% yield) of compound F as a white solid. ESI-LC/MS (M+H)$^+$=482; m.p. 102–105° C.

G.

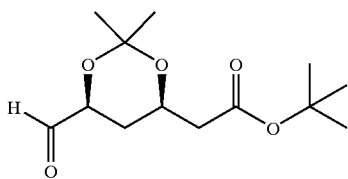

An oven-dried 3-neck 1-L flask equipped with temperature sensor probe, 125-mL constant pressure addition funnel and septum was charged with dry $CH_2Cl_2$ (300 mL) and dry DMSO (20.9 mL, 0.2944 mol, 2.5 equiv) under argon atmosphere; cooled to −7° C. Added neat oxalyl chloride (13.6 mL, 0.156 mol, 1.32 equiv) via syringe dropwise over 15 min (temperature rose to −66° C.), then let stir additional 15 min. A solution of the starting alcohol 2-[(4R,6S)-6-(hydroxymethyl)-2,2-dimethyl-1,3-dioxan-4-yl]acetic acid t-butyl ester (30.66 g, 0.1178 mol, 1 equiv) in dry $CH_2Cl_2$ (80 mL) was added dropwise from the addition funnel over 30 min (temperature rose to −68° C.). The resulting white mixture was stirred for 70 min at −76° C., then added triethylamine (82 mL, 0.5889 mol, 5 equiv) dropwise from addition funnel over 35 min (temperature rose to −65° C.), then stirred the light yellow mixture vigorously at −76° C. TLC ($SiO_2$, 20% $EtOAc/CH_2Cl_2$, Rf=0.52). After 30 min, removed the cooling bath and quenched the reaction by slowly adding cold 20% aq $KH_2PO_4$ (35 mL), followed by cold $H_2O$ (300 mL); let stir 15 min (temperature rose to −7° C.). Poured into 2-L separatory funnel and extracted with hexanes (500 mL). Washed the organic extract with cold 10% aq $KH_2PO_4$ (3×300 mL) and saturated aqueous NaCl (300 mL). Dried the organic over anhydrous $Na_2SO_4$, filtered and concentrated in vacuo to give yellow oil. Purification by $SiO_2$ flash chromatography (10 cm×20 cm column) with 35:65 EtOAc/Hexanes afforded the title compound as a white solid (22.2 g, 0.0859 mol, 73%):

$^1$H NMR ($CDCl_3$) δ1.267–1.465 (m, 16H), 1.802 (dd, J=12.7 Hz, 2.2 Hz, 1H), 2.290–2.464 (m, 2H), 4.314 (d, J=18.4 Hz, 2H), 9.555 (d, J=1.3 Hz, 1H).

H.

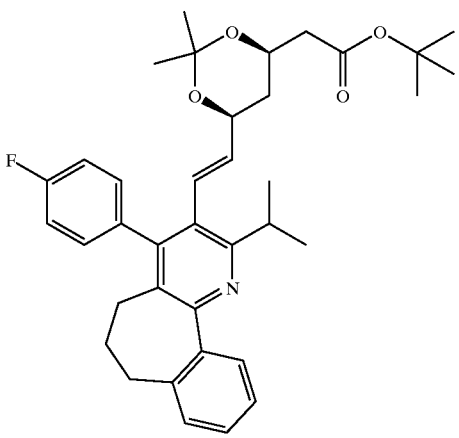

To a cooled (−78° C.) solution of compound F (2.02 g, 4.19 mmol) in anhydrous THF (30 mL) under argon was slowly added a 2.5 M THF solution of n-butyllithium (2.1 mL) over a period of 40 minutes. The temperature was maintained below −75° C. during the addition. After the addition was complete, the reaction mixture was stirred for another 40 minutes at −78° C. A solution of compound G (2.2 g, 8.52 mmol) in THF under argon was cannulated into the phosphonate mixture at −78° C. After the addition was complete, the reaction was stirred for 1 hour at −78° C. The reaction was then warmed to −10° C. and stirred for 1 hour and then stirred at room temperature for an additional hour. The mixture was quenched with saturated ammonium chloride solution (5 mL) and extracted with ethyl acetate (60 mL×3). The combined organic layers were washed with water (10 mL) and brine (10 mL), then dried over sodium sulfate ($Na_2SO_4$) and filtered. The filtrate was concentrated in vacuo. Flash chromatography using 5% to 10% ethyl acetate in hexane as eluent afforded 1.48 g (60% yield) of compound H as a white solid. ESI-LC/MS (M+H)$^+$=586; m.p. 148–149° C.

I.

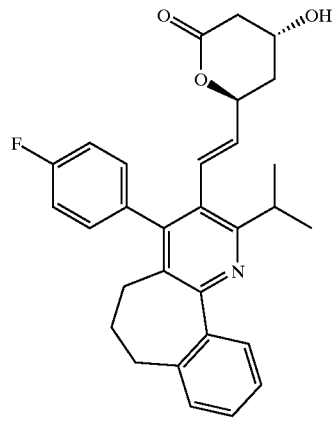

To a cooled (0° C.) solution of compound H (500 mg, 0.854 mmol) in anhydrous $CH_2Cl_2$ (12 mL) under argon was slowly added trifluroacetic acid (987 mL, 12.82 mmol). After the addition was complete, the reaction mixture was allowed to stirred at 0° C. for 10 minutes and at room temperature for 3 hours and then the solvent was removed in vacuo. The reaction mixture was quenched with phosphate solution (pH 7.5, 12 mL) and extracted with $CH_2Cl_2$ (20 mL×2). The combined organic layers were washed with brine (10 mL), dried over sodium sulfate ($Na_2SO_4$), and filtered. The solvent was removed in vacuo. Flash silica gel chromatography using 30% to 50% ethyl acetate in hexane as an eluent afforded 331 mg (80% yield) of compound I as a white powder. ESI-LC/MS (M+H)$^+$=588; m.p. =199–200° C.

J.

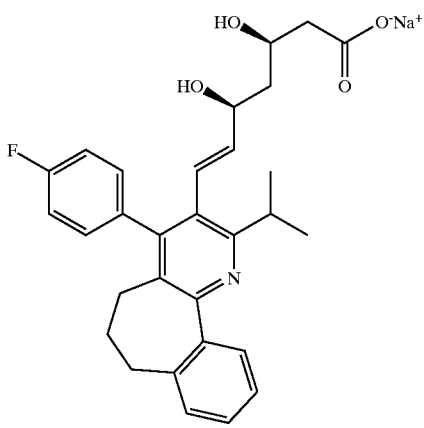

To a solution of compound I (316 mg, 0.671 mmol) in anhydrous THF (6 mL) at room temperature was added an aqueous solution of sodium hydroxide (1N NaOH, 839 µl, 0.839 mmol). The reaction was stirred at room temperature for 10 minutes. The solvent was removed in vacuo and taken up in water (5 mL). The solution was chromatographed on SP-207 resin eluting with water, followed by 25%–40% acetonitrile in water. The desired fractions were stripped, redissolved in water and lyophilized to give title compound (308 mg, 94% yield) as a white solid. ESI-LC/MS (M+H)$^+$= 490; ESI-MS (M+H)+=490;

$^1$H NMR (DMSO-D6; 400 mHz) δ0.97–1.01 (m, 1H), 1.24–1.46 (m, 7H), 1.73–1.78 (m, 1H), 1.93–2.05 (m, 5H), 2.49–2.52 (m, 2H), 3.40–3.53 (m, 2H), 4.03–4.08 (m, 1H), 5.34 (dd, 1H, J =5.72, 10.56 Hz), 6.29 (d, 1H, J =16.24 Hz), 7.21–7.19 (m, 5H), 7.32–7.42 (m, 2H), 7.71 (d, 1H, J=7.48 Hz);

$^{13}$C NMR (DMSO-D6, 400 mHz) δ175.6, 162.5, 161.3, 160.1, 154.2, 147.8, 140.5, 138.8, 134.5, 130.7, 130.5, 129.6, 128.5, 128.1, 126.3, 115.1, 114.9, 68.2, 66.6, 43.7, 43.3, 38.4, 32.3, 30.6, 30.1, 26.4, 24.8, 22.8, 22.7. Anal. Calcd for $C_{30}H_{32}NO_4FNa \cdot 0.9 H_2O$: C, 68.14; H, 6.44; N, 2.65; F, 3.59; Na, 4.35. Found: C, 67.79; H, 5.97; N, 2.51; F, 3.86; Na, 4.83.

EXAMPLE 2A

Alternate Procedure for Example 2 Part H Compound

H(1).

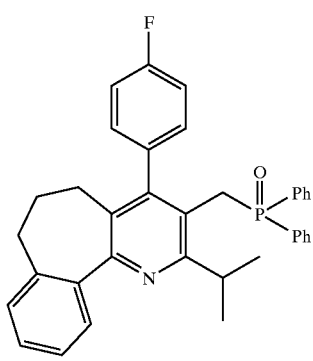

To a stirred solution of Example 2 Part E compound (3.34 g, 7.9 mmol) in toluene (40 mL) was added O-ethyl diphenylphosphinate (2.65 g, 11.5 mmol) in one portion. The reaction was heated to reflux for 2 h, then cooled to room temperature. The white precipitate was collected via filtration and washed with heptane. The residue was dried in vacuo overnight to give title compound as a white solid, 4.3 g, 99% yield, mp 264–265° C.

H(2).

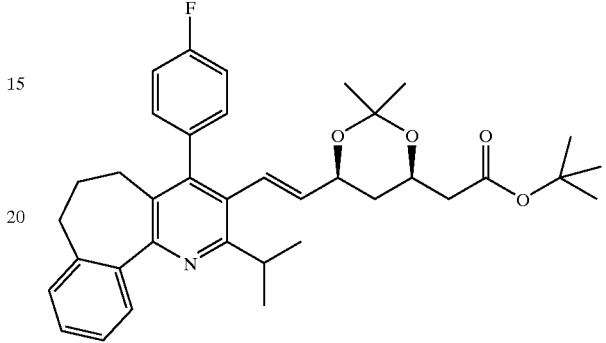

To part H(1) compound (109 mg, 0.2 mmol) in 25 mL 2-necked round bottom flask (flame-dried and fitted with an argon-filled balloon, vacuum take-off and a thermocouple) was added 0.5 mL of DMPU (distilled over $CaH_2$ under reduced pressure, stored with 4A molecular sieves). The resulting slurry was warmed while stirring until becoming a clear solution, which was diluted with THF (1.5 mL). The reaction mixture was evacuated and purged three times with argon, then cooled to −78° C. To the cooled reaction mixture was added dropwise 0.42 mL of a 0.5 M solution of LDA in THF[1] (0.21 mmol). An amber colored solution formed. After stirring at −78° C. for 30 minutes, a solution of Example 2 Part G aldehyde (67 mg, 0.26 mmol) in THF (0.5 mL) was added via a syringe. After addition, the resulting yellow solution was stirred at −78° C. for 30 minutes, then at 0° C. for 1 hour before quenched with an aqueous solution of ammonium chloride. The reaction mixture was extracted three times with ethyl acetate (10 mL). The organic extracts were combined, washed with water and brine, dried (MgSO$_4$) and evaporated. The crude product was purified using flash chromatography on silica gel eluting with 5% EtOAc/hexane. The desired fractions were pooled and concentrated, and the collected residue dried in vacuo overnight to give Part H(2) compound as a white foam, 80 mg (68% yield).

[1]A stock solution of 0.5 M LDA in THF was prepared from diisopropylamine (redistilled, Aldrich) and 2.5 M of BuLi in hexane (Aldrich) following the usual procedures and stored at −20° C.

EXAMPLE 3

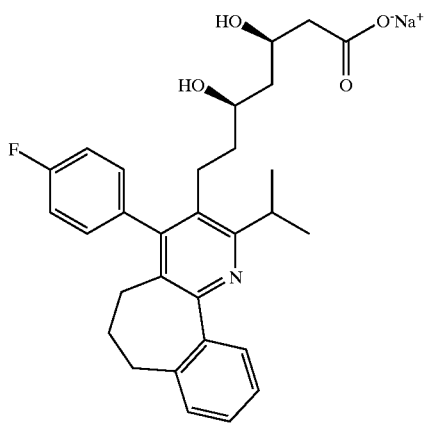

A.

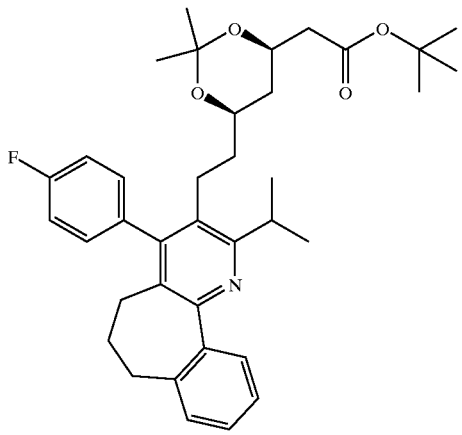

To a solution of Example 2 Part H compound (500 mg, 0.854 mmol) in a mixture of MeOH and EtOH (10 mL) was added 10% Palladium/C (100 mg) and purged with hydrogen ($H_2$). The reaction mixture was then stirred at 55 psi under hydrogen for 2 hours. Upon the completion of the reaction, the catalyst was filtered and the solvent was removed in vacuo to afford 500 mg (99% yield) of the product as a white foam. ESI-LC/MS $(M+H)^+$=588.

B.

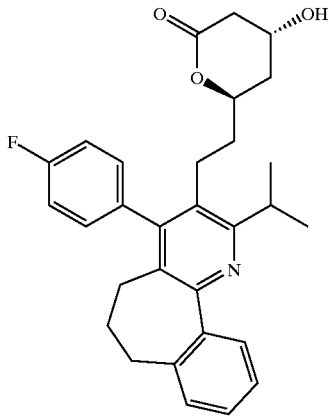

To a cooled (0° C.) solution of Part A compound (450 mg, 0.766 mmol) in anhydrous $CH_2Cl_2$ (9 mL) under argon was slowly added trifluroacetic acid (886 mL, 12.5 mmol). After the addition was complete, the reaction mixture was allowed to stirred at 0° C. for 10 minutes and at room temperature for 3 hours and then the solvent was removed in vacuo. The reaction mixture was quenched with phosphate solution (pH 7.5, 12 mL) and extracted with $CH_2Cl_2$ (20 mL×2). The combined organic layer was washed with brine (saturated NaCl solution, 10 ml), dried over sodium sulfate ($Na_2SO_4$) and filtered. The solvent was removed in vacuo. Flash silica gel chromatography using 30% to 50% ethyl acetate in hexane as an eluent afford 330 mg (91% yield) part B compound as a white powder. ESI-LC/MS $(M+H)^+$=474, MP (° C.)=253–254.

C.

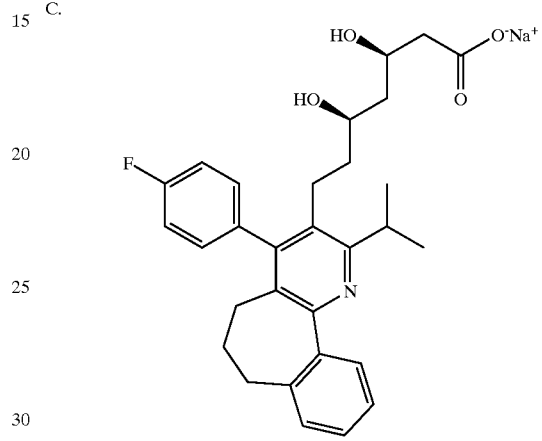

To a solution of part B compound (330 mg, 0.698 mmol) in anhydrous THF (8 mL) at room temperature was added an aqueous solution of sodium hydroxide (1N NaOH, 872 µl, 0.872 mmol). The reaction was stirred at room temperature for 10 minutes. The solvent was removed in vacuo and taken up in water (5 mL). SP-207 resin bound chromatography using water, followed by 20% to 40% acetonitrile in water as the eluent afford 315 mg (92% yield) of Part C compound as a white lyophillate. The SP-207 resin was pre-washed with saturated sodium bicarbonate solution ($NaHCO_3$, 50 mL) followed by saturated sodium chloride solution (NaCl, 50 mL), and water (200 mL).

ESI-LC/MS $(M+H)^+$=492, ESI-MS (M+H)+=492;

$^1$H NMR (DMSO-D6; 400 mHz) δ1.05–1.09 (m, 1H), 1.23–1.29 (m, 8H), 1.35–1.44 (m, 2H), 1.70–1.78 (m, 1H), 1.90–1.98 (m, 6H), 2.25–2.35 (m, 1H), 2.45–2.55 (m, 1H), 3.36–3.40 (m, 1H), 3.62–3.65 (m, 1H,), 4.70 (s, 1H), 7.25–7.41 (m, 7H), 7.67 (d, 1H, J=7.48 Hz);

$^{13}$C NMR (DMSO-D6, 400 mHz) δ175.8, 162.4, 160.6, 160.0, 155.0, 146.8, 141.0, 140.3, 138.9, 134.7, 131.2, 130.9, 129.5, 128.8, 128.3, 126.3, 68.6, 65.6, 44.7, 44.3, 40.0, 32.6, 31.1, 30.6, 26.3, 22.2.

Following the procedure of Examples 1 to 3 the following compounds may be prepared.

Examples 4 to 18

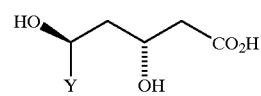

where Y is as set out below

Example 4
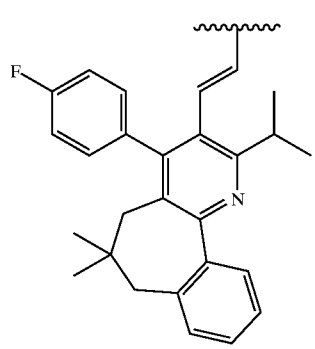
Example 5
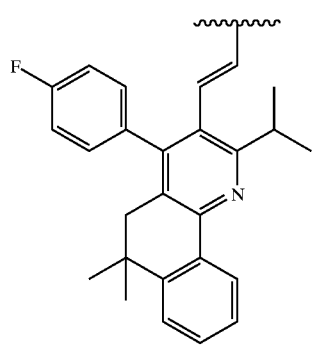
Example 6
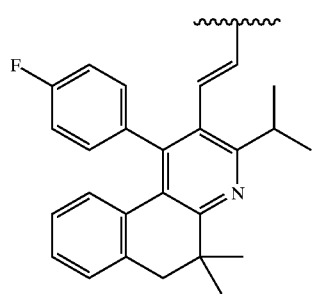
Example 7
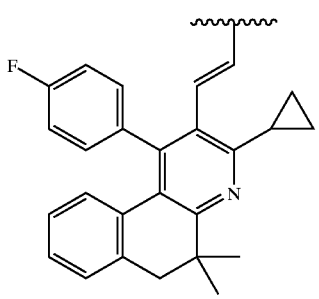
Example 8
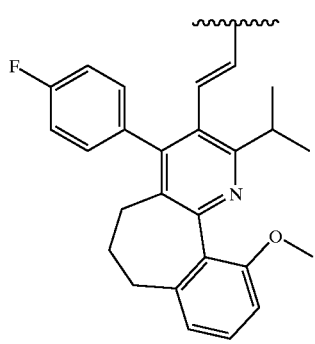
Example 9
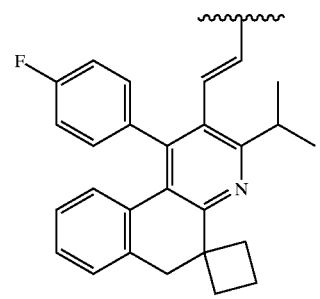
Example 10
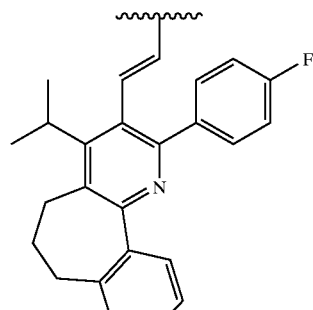
Example 11
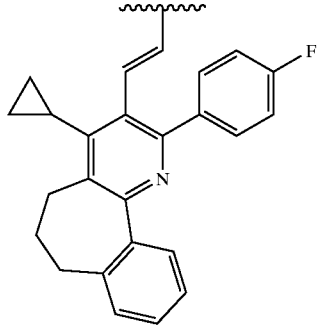
Example 12
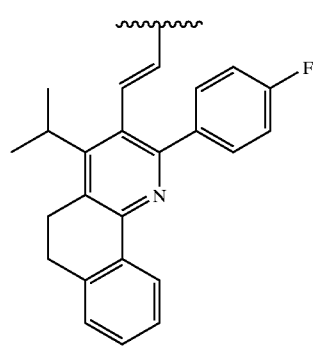
Example 13
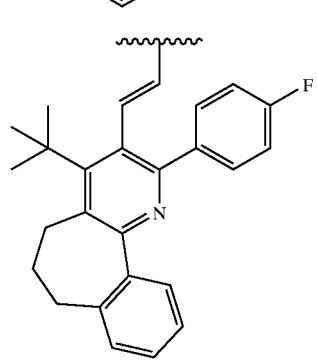

-continued
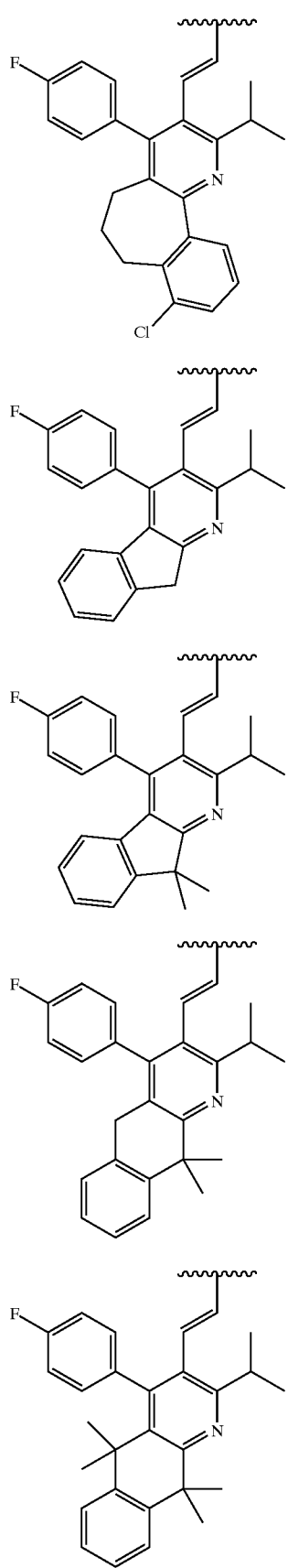
Example 14
Example 15
Example 16
Example 17
Example 18
-continued
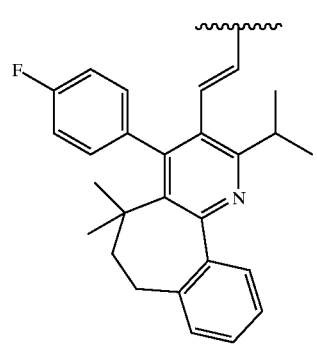
Example 19
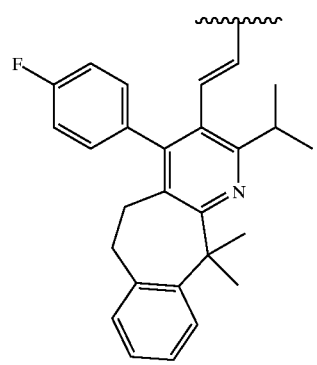
Example 20
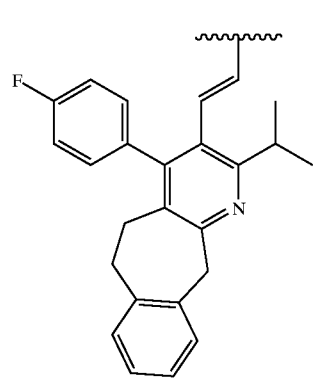
Example 21
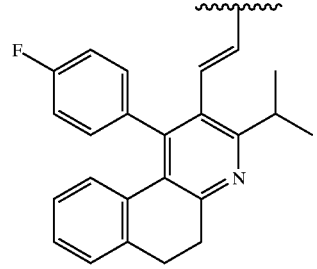
Example 22
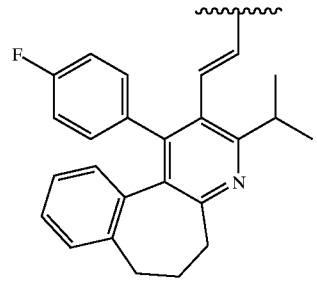
Example 23

-continued
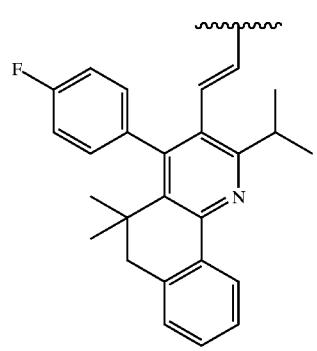
Example 24
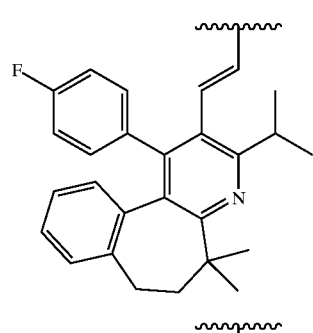
Example 25
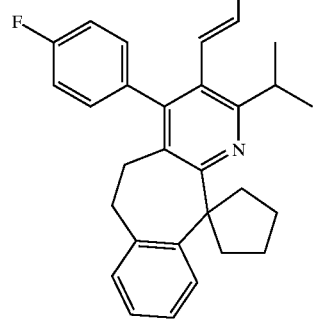
Example 26
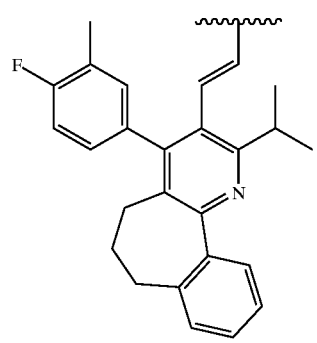
Example 27
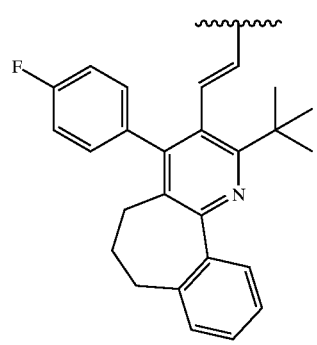
Example 28
-continued
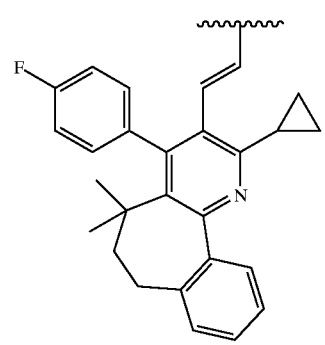
Example 29
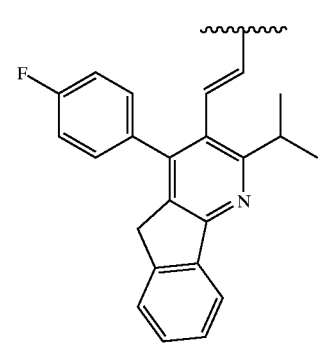
Example 30
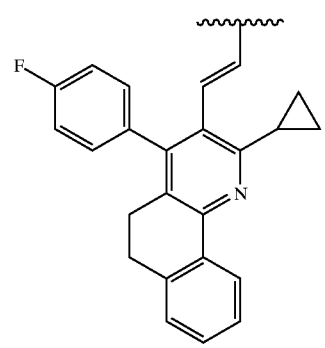
Example 31
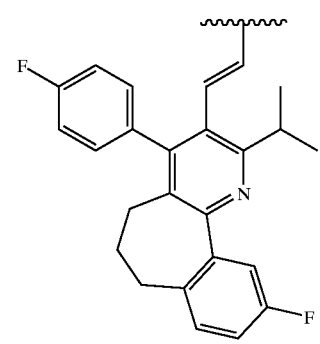
Example 32

-continued

Example 33

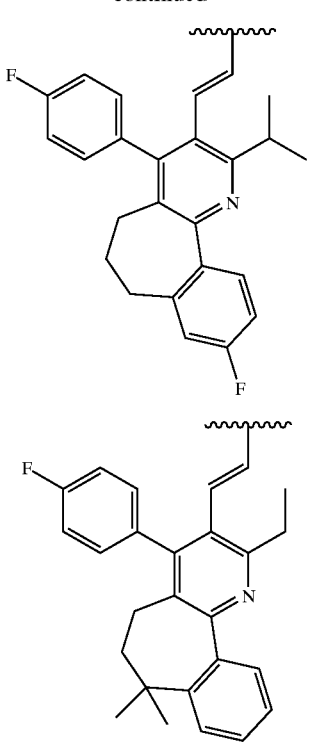

Example 34

It will be appreciated that the compounds of Examples 1 to 34 may also be converted to corresponding lactones and/or salts thereof.

With respect to Examples 35 to 38, please refer to Scheme 6.

EXAMPLE 35

Preparation of Pyridine Aldehyde (18) (Scheme 6)

A.

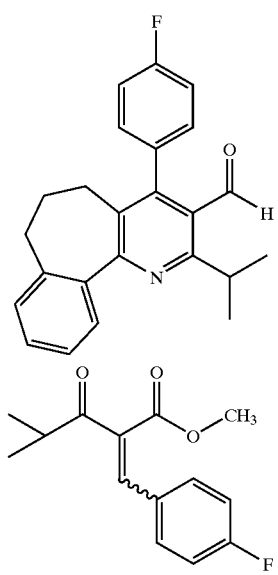

To a mixture of 4-fluoro-benzaldehyde (935.8 g, 7.54 moles) and methyl isobutyryl acetate (1087 g, 7.54 moles) was added piperidine (64.2 g, 0.75 mol), followed by acetic acid (22.6 g, 0.38 mol). The mixture was heated to 80 to 85° C. for about 2 hours. 16 Liters (4×4L) of toluene was added and mixed with the reaction mixture. The toluene was removed using a rotavapor (50–65° C./20–90 torr), leaving a yellow oil. The yellow oil was dissolved in 5 L MTBE and washed with:

1×3 L HCl (0.5N)
1×3 L NaHCO$_3$ (saturated soln.)
1×3 L DI water

The MTBE was evaporated off. Thereafter, 1.5 L of MTBE was added and the mixture evaporated to remove water to afford about 1780 g (yield 88%) of title compound as a yellow oil.

B.

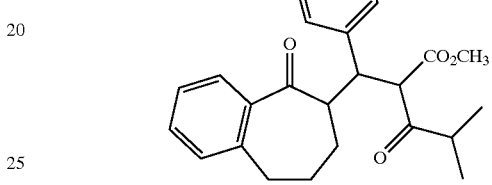

To 7.35 L NaHMDS(7.35 moles, 1.05 eq) under N$_2$ (cooled down between −72 to −65° C.) was added a THF (6 L) solution of 1-benzosuborone (1177 g, 7.35 moles, 1.05 eq). The reaction temperature was maintained below −50° C. during the addition. The reaction was then stirred at—between −72 to −65° C. for 1 hour and a solution of compound A (1751.5 g, 7.0 moles, in 6 L THF) was slowly added to the reaction while keeping the temperature below −50° C. After the addition was complete, the reaction was stirred for 2–3 hours between −72 to −65° C. The reaction was quenched with HOAc (1.4 L) between −72 to −50° C. The mixture was allowed to reach RT and saturated ammonium chloride solution (NH$_4$Cl,15 L) was added plus 7 L DI-water, and the mixture agitated for 5–10 min. The aqueous layer was extracted with 1×8 L MTBE. The combined organic layers were washed with water (2×9 L) and brine (1×9 L), then dried. The solvent was removed to afford crude compound B (3.08 kg). The crude compound B was used directly in the next step.

C.

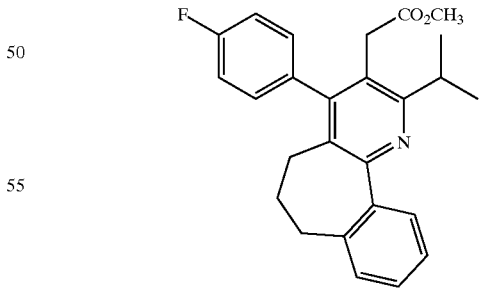

To a solution of the crude compound B (3078 g) in aqueous HOAc (16 L) was added ammonium acetate (1446 g), followed by cupric acetate monohydrate (1859 g). The reaction was refluxed between 120 to 124° C. for 12–15 hours. Approximately 90% of the acetic acid was evaporated to produce a green slurry. The slurry was then mixed with 14 L MTBE.

The resulting solution was filtered through a celite pad (177 g celite in a 7"×8", W$_x$H, funnel) and the cake washed with 16 L MTB. The organic phase was washed with:

2×9 L DI-water, pH of combined wash=4.2
2×3 L NaHCO$_3$, pH of the combined wash=6.4
1×9 L DI-water, pH=6.0.

The solvent was evaporated to produce a black oil (2883 g). 2.5 L of methanol was added and the mixture agitated for approximately 2–3 h. The product was filtered and washed with 2 L of cold methanol (−10 to 0° C.). The product was dried at 40–50° C./~20" of Hg to produce an off-white solid, 793 g, HPLC AP=97.8. Yield=27%.

D.

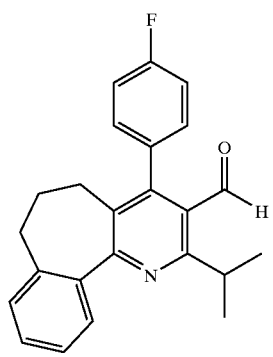

(18)

To a 500 mL round bottom flask equipped with a magnetic stirrer and a nitrogen inlet was charged Part C compound (17) (Scheme 6) (50.0 g, 128.4 mmol) and toluene (170 mL). The mixture was stirred at 20–25° C. until a clear solution was obtained. A solutin of 65% Red-Al in toluene (57.8 mL, 192.6 mmol) was added and the reaction mixture was heated to 80° C. until complete as determined by HPLC. The reaction mixture was cooled to ~20° C. and quenched by pouring it into cold (0–5° C.) 20% HCl (495 mL). Phases were separated and the spent toluene phase was discarded. The pH of the aqueous phase was adjusted from <0 to 4–5 with 10N NaOH. Ethyl acetate (500 mL) was added and the pH adjustment continued to 7–8. The phases were separated. The aqueous phase was extracted with additional ethyl acetate (2×500 mL). The combined rich ethyl acetate solution was washed with water (3×250 mL) and concentrated under reduced pressure to ~465 mL. This solution was carried through to the next oxidation step.

The rich ethyl acetate solution was charged from above into a three neck 1-L flask equipped with mechanical stirring, temperature controller, and addition funnel and cooled to 0–5° C. To the slurry, potassium bromide (1.53 g, 12.8 mmol) and TEMPO (2,2,6,6-tetramethyl-1-piperidinyloxy) (0.20 g, 1.28 mmol) were added. The pH of NaOCl (sodium hypochlorite) solution (212.1 mL) was adjusted to 9.1 and added to the slurry at a rate such that the temperature remained at 0–5° C. Stirring was continued at 0–5° C. until the reaction was complete as determined by HPLC. The aqueous phase was extracted with EtOAc (2×200 mL). The combined rich organic phase was washed with a 1:1 solution of sat. aq. Na$_2$S$_2$O$_3$ (sodium thiosulfate) (75 mL) and water (75 mL) followed by wash of the rich organic phase with 1N NaOH (250 mL). The rich organic phase was washed with water (250 mL) and concentrated to ~100 mL under reduced pressure. Isopropanol (IPA) (400 mL) was added and the resulting mixture was heated to reflux (80–85° C.). The solution was distilled to a volume of ~250 mL. Water (50 mL) was added and the crystal slurry was stirred at 70–80° C. for 1 h then allowed to cool to 20–25° C. over at least 1 h. The slurry was held at 20–25° C. for at least 1 h before collecting the solid by filtration on a Buchner funnel. The cake was washed with cold (0° C.) IPA/water (4:1) (2×50 mL) and dried to a constant weight under vacuum at 40° C. to afford 41.5 g (90%) of title aldehyde as a white crystalline solid.

EXAMPLE 36

(Scheme 6)

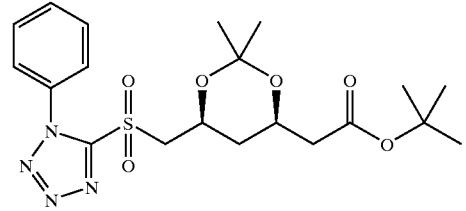

(16)

A. Preparation of Sulfide (15)

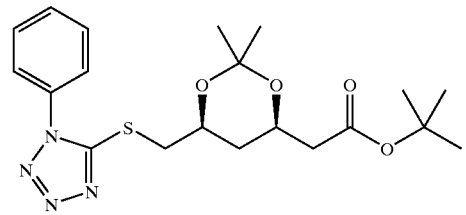

(15)

To a 250 mL flask was charged Kaneka alcohol (12) (Scheme 6) (10.0 g, 38.41 mmol), methylene chloride (100 mL), and triethylamine (11.75 mL, 84.51 mmol) and cooled to −30° C. Triflic anhydride (7.11 mL, 42.25 mmol) was added via a syringe at a rate to maintain the temperature at −35 to −25° C., ~15 min. The reaction mixture was stirred at −30° C. for ~30 min and checked for disappearance of Kaneka alcohol by TLC. A slurry of 1-phenyl-1H-tetrazole-5-thiol (7.19 g, 40.34 mmol) in methylene chloride (50 mL) was added to the triflate solution. After the reaction was complete, water(100 mL) was added and the mixture was stirred for ~5 min. The phases were separated and the aqueous phase was discarded. The rich organic phase was washed with water (100 mL) for ~5 min and phases separated. The rich organic phase was washed with saturated NaHCO$_3$ (100 mL) for ~15 min and phases separated. The rich organic phase was concentrated to ~50 mL. The solution was taken to the next step for further transformation.

B. Preparation of Sulfone (16)

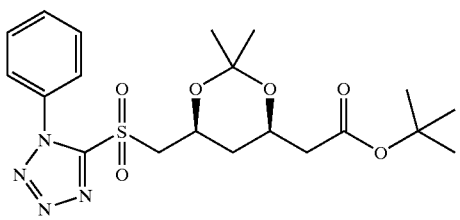

IPA (150 mL) was added to the Part A sulfide solution from the above step. The solution was cooled to 0–5° C. To the stirred solution of sulfide, a solution of $(NH_4)_6 MO_7O_{24} \cdot 4H_2O$ (ammonium heptamolybdate tetrahydrate) (4.75 g, 3.84 mmol) in 30% $H_2O_2$ (hydrogen peroxide) was added dropwise during ~15 min, maintaining the temperature of the solutin at 0–5° C. The conversion of sulfide to sulfone was monitored by HPLC ~24 h. After completion of the reaction, methylene chloride was distilled out. The pot temperature was maintained at not more than 25° C. The crystal slurry was distilled to a volume of ~230 mL with IPA and the resulting slurry was stirred for at least 1 h at 20–22° C. The solid was collected by vacuum filtration, the cake washed with IPA/water (4:1, 25 mL) followed by drying under vacuum at 40° C. to constant weight affording 12.8 g (74%) of the title sulfone as a white crystalline solid.

mL). The stirred solution was cooled to −74 to −78° C. Slowly a 1M solution of LIHMDS (lithium bis(trimethylsilyl)amide) (15.3 mL, 15.3 mmol) in THF was charged at a rate such that the temperature remained between −70 and −78° C. After addition of the base was complete, the reaction mixture was warmed to ~−45° C. over ~15 minutes. The stirred reaction was quenched at −70° C. by slow addition of sat. aq. $NH_4Cl$ (7.5 mL) solution and water (38 mL). The dry ice bath was removed and the solution was warmed to 20–25° C. from the reaction mixture. Ethyl acetate (50 mL) was added, the mixture agitated, and layers separated. The organic layer was washed with saturated sodium bicarbonate solution (2×38 mL) followed by brine (25 mL) and concentrated to a volume of 50 mL. Acetonitrile (50 mL) was added and the solution was concentrated to a volume of 50 mL. This step was repeated. Water (~5–6 mL) was slowly added to the hot solution (60–70° C.) until the cloud point was reached. The thin slurry was held for 30 min at high temperature and then slowly cooled over several hours with stirring. The product was filtered, cake was washed with a 5:1 mixture of acetonitrile and water, and dried to afford 7.5 g (91%) of the title compound as a white crystalline material.

EXAMPLE 38

Preparation of the Final Compound as Arginine Salt ($Ib^9$)

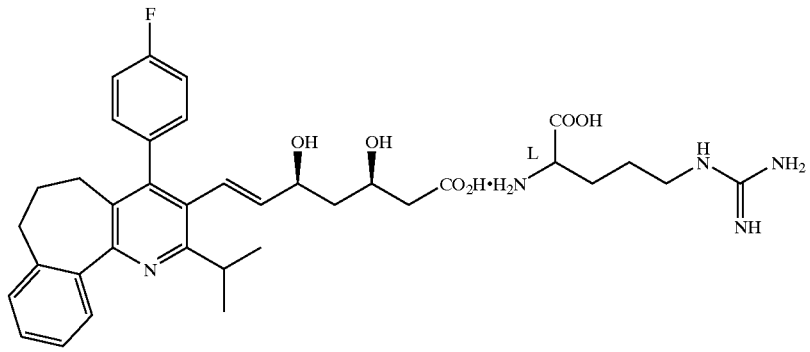

EXAMPLE 37

Preparation of Olefin (19)

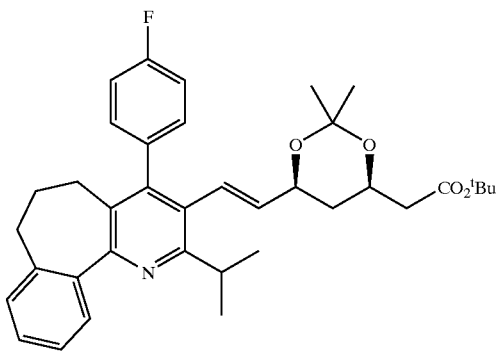

A $N_2$ purged 250 mL 3-neck rb flask was charged with Example 35 pyridine derivative (18) (5.0 g, 13.9 mmol), Example 36 sulfone (16) (6.92 g, 15.3 mmol) and THF (75

To a 3.0-liter round bottom flask equipped with a mechanical stirrer, a thermometer, and a septa was charged Example 37 trans olefin (19) (92.0 g, 157 mmol) and THF (600 mL) at ambient temperature. With stirring, to the resulting clear sight yellow solution was added 6N HCl (aq. 74.6 mL, 447 mmol) at ambient temperature to form (20);

(20)

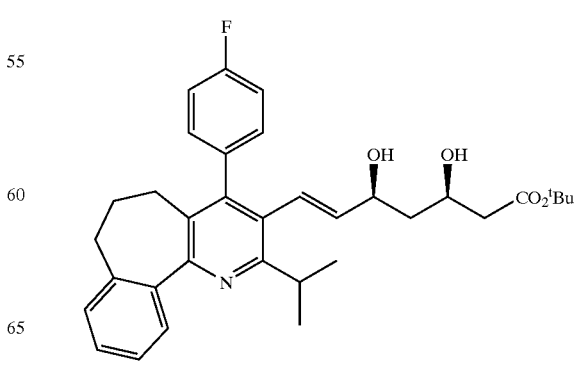

The reaction mixture was stirred for 5.0–6.0 h followed by addition of 2 N NaOH (aq. 389 mL, 777 mmol) to form a light yellow suspension. Agitation was maintained at ambient until reaction (saponification of (20)) was judged complete by an in-process HPLC assay. THF was evaporated on a rotary evaporator at about 45° C. The white slurry residue was diluted with 1000 mL of water and was extracted with MTBE (methyl t-butyl ether) (230 mL×2). After separating the MTBE layer, the aqueous layer containing (21):

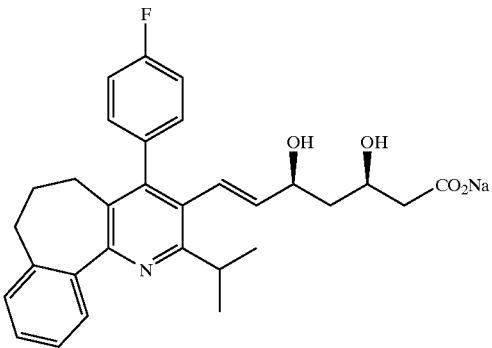

was transferred to a 5.0-liter round bottom flask equipped with a mechanical stirrer, a thermometer, and a septa. While temperature was controlled at <29° C., 1 N HCl (aq) was added to the above aqueous layer until the pH=6.94. Subsequently, 330 mL of ethyl acetate was added to the aqueous layer followed by charging more 1 N HCl (aq) until pH=2.82. After separating and saving the ethyl acetate layer, the aqueous layer was extracted with ethyl acetate (330 mL×3). The combined ethyl acetate layers containing acid Ib$^8$ of the invention:

(Scheme 6)

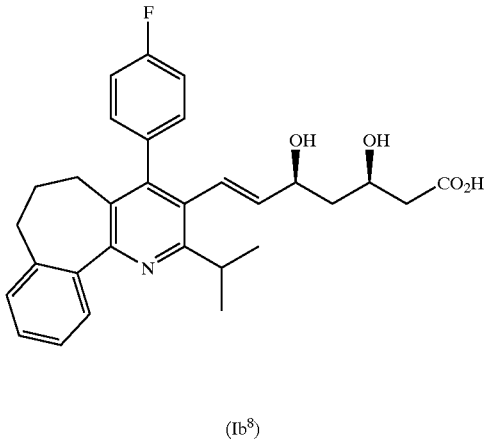

(Ib$^8$)

were washed with 50% brine (265 mL), brine (427 mL), separated and mixed with a suspension of L-arginine (27.4 g, 157 mmol) in ethanol (276 mL) and water (138 mL). The mixture was evaporated to dryness under reduced pressure at ca 45–50° C. To the resulting white solid were added ethyl acetate (450 mL), ethanol (316 mL), and water (145 mL) followed by heating the white suspension to 50° C. Another 36.7 mL of water was added to dissolve all solids at 56° C; subsequently 1720 mL of ethy acetate was added to the hot solution to initialize the crystallization. The white suspension was stirred at 50° C. for 1.5 h and at ambient for 13 h. After filtration, the crystalline solid was washed with 143 mL of a mixture of EtOAc (200 mL), EtOH (12 mL) and $H_2O$ (6 mL) and was dried in vacuo at 40–50° C. for 24 h. The title product obtained as a white solid weighed 78.9 (g). Yield, 75.7%. $[\alpha]^{25}_D$=+23.0 (c 0.31, $CH_3CN:H_2O$, 1:1, v/v).

$^1$H NMR ($CD_3OD$): δ7.74 (dd, J=2.5 Hz, J"=1.0 Hz, 1H), 7.41 (dt, J=7.0 Hz, J'=6.1 Hz, 1H), 7.37 (dt, J=7.3 Hz, J'=1.4 Hz, 1H), 7.27 (d, J=7.2 Hz, 1H), 7.22 (dd, J=15.4 Hz, J'=7.0 Hz, 2H), 7.20 (d, J=7.0 Hz, 2H), 6.45 (d, J=16.5 Hz, 1H), 5.43 (dd, J=16.5 Hz, J'=6.5 Hz, 1H), 4.24 (q, J=6.5 Hz, 1H), 3.79 (m, 1H), 3.55–3.50 (m, 2H), 3.23 (m, 2H), 2.62 (t, J=7.2 Hz, 2H), 2.31–2.21 (m, 2H), 2.16 (t, J=6.8 Hz, 2H), 2.05 (m, 2H), 1.87 (q, J=7.0 Hz, 2H), 1.74 (m, 2H), 1.57 (m, 1H), 1.34 (d, J=6.8 Hz, 6H), 1.31 (m, 1H).

$^{13}$C NMR ($CD_3OD$): δ180.1, 174.7, 164.5, 163.1, 162.5, 158.7, 157.8, 149.1, 141.9, 141.0, 140.8, 136.4, 132.6, 132.3, 131.6, 130.5, 130.1, 129.7, 129.2, 127.6, 126.6, 116.3, 116.0, 71.5, 68.0, 55.6, 45.0, 41.9, 34.2, 33.1, 32.2, 29.6, 27.7, 25.8, 22.5.

MS: calc'd for $C_{36}H_{46}FN_5O_6$ ($M^++H$) 490 and 175, found 490 and 175.

IR (KBr): 3341, 3200, 3070, 2960, 2934, 2860, 1670, 1629, 1602, 1580, 1509, 1465, 1450, 1397, 1357, 1221, 842, 766, 740 cm$^{-1}$.

Anal. Calc'd for $C_{36}H_{46}FN_5O_6$: C, 65.14; H, 6.98; N, 10.55. Found C, 65.15; H, 6.97; N, 10.53.

What is claimed is:

1. A compound having the structure:

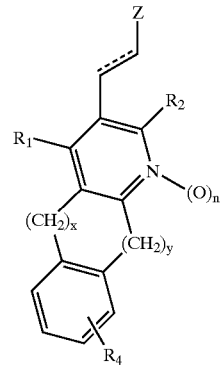

wherein

Z is

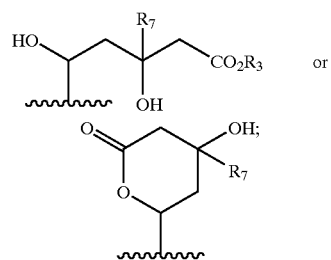

also referred to as the δ-lactone;

n is 0 or 1;

x is 0, 1, 2, 3 or 4;

y is 0, 1, 2, 3 or 4, provided that at least one of x and y is other than 0; and optionally one or more carbons of $(CH_2)_x$ and/or one or more carbons of $(CH_2)_y$ together with additional carbons form a 3 to 7 membered spirocyclic ring;

$R_1$ and $R_2$ are the same or different and are independently selected from alkyl, arylalkyl, cycloalkyl, alkenyl, cycloalkenyl, aryl, heteroaryl or cycloheteroalkyl;

$R_3$ is H or lower alkyl;

$R_4$ is halogen, $CF_3$, hydroxy, alkoxy, carboxyl, carboxyalkyl-, aminoalkyl, amino, alkanoylamino, aroylamino, cyano, alkoxyCON($R_{10}$)—, $R_{11}R_{12}NCO_2$—, $R_{11}R_{12}NCO$—, $R_{13}SO_2N(R_{10})$—, $R_{11}R_{12}NSO_2N(R_{10})$—, $R_{13}OCO_2$— or $R_{13}OCO$;

$R_{13}$ is alkyl, arylalkyl, cycloalkyl, alkenyl, cycloalkenyl, aryl, heteroaryl or cycloheteroalkyl;

$R_{11}$ and $R_{12}$, and $R_{10}$ are the same or different and are independently selected from H, alkyl, arylalkyl, cycloalkyl, alkenyl, cycloalkenyl, aryl, heteroaryl or cycloheteroalkyl;

$R_7$ is H or lower alkyl;

and ⫽ represents a single bond or a double bond (which may be cis or trans);

or a pharmaceutically acceptable salt thereof (when $R_3$ is H), or an ester thereof, or a stereoisomer thereof.

2. The compound as defined in claim 1 wherein ⫽ is a double bond which is trans.

3. The compound as defined in claim 1 wherein Z is in the form of a pharmaceutically acceptable basic salt.

4. The compound as defined in claim 1 in the form of a pharmaceutically acceptable acid addition salt.

5. The compound as defined in claim 1 wherein $R_1$ and $R_2$ are independently selected from alkyl, cycloalkyl and aryl;

$R_4$ is halogen;

n is 0;

x is 2 or 3;

and y is 0.

6. The compound as defined in claim 1 wherein $R_1$ is aryl, $R_2$ is alkyl or cycloalkyl;

n is 0;

x is 3;

y is 0; and

⫽ is a trans double bond, in the form of a free acid, an alkali metal salt, or an alkaline earth metal salt, or an amino acid salt.

7. The compound as defined in claim 6 wherein $R_1$ is phenyl which contains 1 or 2 substituents, $R_2$ is alkyl or cycloalkyl; and ⫽ is a trans double bond, in the form of a free acid, an alkali metal salt, or an alkaline earth metal salt or an amino acid.

8. The compound as defined in claim 7 wherein $R_1$ is 4-fluorophenyl, 4-fluoro-3-methylphenyl, or 3,5-dimethylphenyl; and $R_2$ is isopropyl, t-butyl or cyclopropyl.

9. The compound as defined in claim 1 wherein Z has the structure:

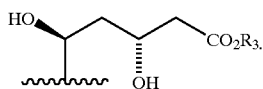

10. The compound as defined in claim 1 having the structure:

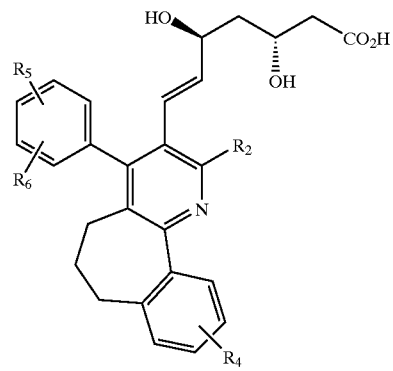

or an alkali metal salt, or an alkaline earth metal salt, or an amino acid salt, or an acid addition salt via the pyridine, or the corresponding δ lactone, wherein $R_5$ and $R_6$ are the same or different and are independently selected from H, halogen or alkyl and $R_2$ is alkyl or cycloalkyl.

11. The compound as defined in claim 10 wherein $R_5$ and $R_6$ are H and 4-fluoro;

H and 4-fluoro-3-methyl or 3,5-dimethyl; and $R_2$ is isopropyl, t-butyl or cyclopropyl.

12. The compound as defined in claim 1 in the form of its calcium salt, sodium salt or arginine salt.

13. A pharmaceutical composition comprising a compound as defined in claim 1 and a pharmaceutically acceptable carrier therefor.

14. A method for treating hypercholesterolemia, dyslipidemia, hyperlipidemia, hyperlipoproteinemia, LDL Pattern B, LDL Pattern A, hypertriglyceridemia or atherosclerosis, or osteoporosis, which comprises administering to a mammalian species in need of such treatment a HMG-CoA reductase inhibiting effective amount of a compound as defined in claim 1.

15. A method of inhibiting cholesterol biosynthesis or lowering blood serum cholesterol levels, lowering LDL cholesterol and/or increasing HDL cholesterol, or treating dyslipidemia, mixed dyslipidemia, LDL Pattern B, LDL Pattern A, hyperlipidemia, hypercholesterolemia, hypo α-lipoproteinemia, hyperlipoproteinemia or hypertriglyceridemia, or reducing levels of Lp(a), or treating atherosclerosis, or treating osteoporosis and/or osteopenia, or reducing inflammatory markers, reducing C-reactive protein, or treating low grade vascular inflammation, stroke, dementia, or coronary heart disease, or preventing primary or secondary myocardial infarction, or treating stable or unstable angina, or preventing primary coronary events, or preventing secondary cardiovascular events, or treating peripheral vascular disease, treating peripheral arterial disease, or treating acute vascular syndromes, or reducing the risk of undergoing myocardial revascularization procedures which comprises administering to a mammalian species in need thereof a HMG-CoA reductase inhibiting effective amount of a compound in accordance with claim 1.

16. A method for treating diabetes, Type 2 diabetes, insulin resistance, hyperglycemia, hyperinsulinemia, elevated blood levels of fatty acids or glycerol, obesity, LDL Pattern B, LDL Pattern A, Syndrome X, diabetic complications, or dysmetabolic syndrome, which com P rises administering to a mammalian species in need of such treatment a HMG-CoA reductase inhibiting effective amount of a compound as defined in claim 1.

17. A method for treating drug-induced lipodystrophy, which comprises administering to a mammalian species in need of such treatment a HMG-CoA reductase inhibiting effective amount of a compound as defined in claim 1.

18. The compound as defined in claim 1 having the structure:

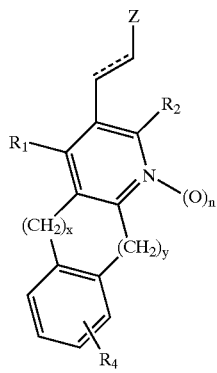

wherein

Z is

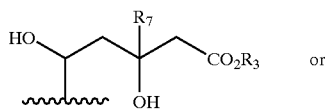

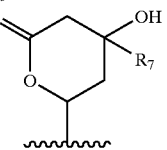

also referred to as the δ-lactone;

n is 0 or 1;

x is 0, 1, 2, 3 or 4;

y is 0, 1, 2, 3 or 4, provided that at least one of x and y is other than 0; and optionally one or more carbons of $(CH_2)_x$ and/or one or more carbons of $(CH_2)_y$ together with additional carbons form a 3 to 7 membered spirocyclic ring;

$R_1$ and $R_2$ are the same or different and are independently selected from alkyl, arylalkyl, cycloalkyl, alkenyl, cycloalkenyl, aryl, heteroaryl or cycloheteroalkyl;

$R_3$ is H or lower alkyl;

$R_4$ is halogen, $CF_3$, hydroxy, alkoxy, alkanoylamino, aroylamino or cyano;

$R_7$ is H or lower alkyl;

and ⫽ represents a single bond or a double bond (which may be cis or trans);

or a pharmaceutically acceptable salt thereof (when $R_3$ is H), or an ester thereof, or a stereoisomer thereof.

* * * * *